United States Patent
Kirsch et al.

(10) Patent No.: US 11,522,141 B2
(45) Date of Patent: *Dec. 6, 2022

(54) ELECTRONIC SWITCHING ELEMENT

(71) Applicant: MERCK PATENT GMBH, Darmstadt (DE)

(72) Inventors: Peer Kirsch, Seeheim-Jugenheim (DE); Andreas Ruhl, Rossdorf (DE); Marc Tornow, Munich (DE); Achyut Bora, Munich (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/340,459

(22) Filed: Jun. 7, 2021

(65) Prior Publication Data
US 2021/0292651 A1 Sep. 23, 2021

Related U.S. Application Data

(62) Division of application No. 16/315,827, filed as application No. PCT/EP2017/066534 on Jul. 4, 2017, now Pat. No. 11,063,227.

(30) Foreign Application Priority Data
Jul. 7, 2016 (DE) ..................... 10 2016 008 207.0

(51) Int. Cl.
*C07C 43/29* (2006.01)
*C07C 59/125* (2006.01)
(Continued)

(52) U.S. Cl.
CPC .......... *H01L 51/0076* (2013.01); *C07C 43/29* (2013.01); *C07C 59/125* (2013.01);
(Continued)

(58) Field of Classification Search
None
See application file for complete search history.

(56) References Cited

U.S. PATENT DOCUMENTS

| 4,973,697 A | 11/1990 | Umemoto et al. |
| 5,217,953 A | 6/1993 | Gozes et al. |

(Continued)

FOREIGN PATENT DOCUMENTS

| CN | 102604652 A | 7/2012 |
| CN | 103214353 A | 7/2013 |

(Continued)

OTHER PUBLICATIONS

Montoneri et al., "Organosulphur Phosphorus Acid Compounds. Part 7. Preparation and Analytical Identification of Difluorobenzylphosphono-Sulfonic Acids", Phosphorus, Sulfur.
(Continued)

*Primary Examiner* — Kevin M Bernatz
(74) *Attorney, Agent, or Firm* — Millen White Zelano & Branigan, PC; Brion P. Heaney

(57) ABSTRACT

An electronic switching element is described having, in sequence, a first electrode, a molecular layer bonded to a substrate, and a second electrode. The molecular layer contains compounds of formula I, $R^1-(A^1-Z^1)_r-B^1-(Z^2-A^2)_s$-Sp-G, wherein $A^1$, $A^2$, $B^1$, $Z^1$, $Z^2$, Sp, G, r, and s are as defined herein, in which a mesogenic radical is bonded to the substrate via a spacer group, Sp, by means of an anchor group, G. The switching element is suitable for production of components that can operate as a memristive device for digital information storage.

12 Claims, 10 Drawing Sheets

(51) Int. Cl.
| | |
|---|---|
| C07F 9/38 | (2006.01) |
| C09K 19/12 | (2006.01) |
| C09K 19/30 | (2006.01) |
| C09K 19/60 | (2006.01) |
| C09K 19/40 | (2006.01) |
| H01L 51/00 | (2006.01) |
| G11C 13/00 | (2006.01) |
| H01L 27/28 | (2006.01) |
| H01L 27/24 | (2006.01) |
| H01L 45/00 | (2006.01) |
| H01L 51/05 | (2006.01) |
| H01L 51/10 | (2006.01) |

(52) U.S. Cl.
CPC ............ *C07F 9/386* (2013.01); *C07F 9/3808* (2013.01); *C07F 9/3839* (2013.01); *C09K 19/12* (2013.01); *C09K 19/3003* (2013.01); *C09K 19/404* (2013.01); *C09K 19/60* (2013.01); *G11C 13/0016* (2013.01); *G11C 13/0069* (2013.01); *H01L 27/24* (2013.01); *H01L 27/285* (2013.01); *H01L 45/12* (2013.01); *H01L 45/14* (2013.01); *C07C 2601/14* (2017.05); *C09K 2019/122* (2013.01); *C09K 2019/301* (2013.01); *G11C 2013/009* (2013.01); *G11C 2213/35* (2013.01); *G11C 2213/52* (2013.01); *H01L 51/0591* (2013.01); *H01L 51/105* (2013.01); *Y10T 428/1114* (2015.01)

(56) References Cited

U.S. PATENT DOCUMENTS

| | | | |
|---|---|---|---|
| 6,217,953 B1 | 4/2001 | Heckmeier et al. | |
| 6,475,595 B1* | 11/2002 | Bremer | C09K 19/3402 252/299.61 |
| 7,018,685 B2 | 3/2006 | Schmidt et al. | |
| 7,166,238 B2 | 1/2007 | Kato et al. | |
| 8,475,889 B2 | 7/2013 | Klasen-Memmer et al. | |
| 8,895,117 B2 | 11/2014 | Jansen et al. | |
| 8,975,622 B2* | 3/2015 | Hayashi | H01L 45/14 257/40 |
| 9,117,749 B1 | 8/2015 | Or-Bach et al. | |
| 9,172,053 B2 | 10/2015 | Hayashi et al. | |
| 9,234,136 B2 | 1/2016 | Archetti et al. | |
| 9,347,000 B2 | 5/2016 | Jansen et al. | |
| 9,515,195 B2 | 12/2016 | Nishizawa et al. | |
| 9,653,159 B2 | 5/2017 | McCreery et al. | |
| 9,726,933 B2 | 8/2017 | Archetti et al. | |
| 9,837,439 B1 | 12/2017 | Faul | |
| 9,982,194 B2 | 5/2018 | Klasen-Memmer et al. | |
| 10,273,409 B2 | 4/2019 | Graziano et al. | |
| 10,301,545 B2 | 5/2019 | Archetti et al. | |
| 10,358,601 B2 | 7/2019 | Bae et al. | |
| 10,669,483 B2 | 6/2020 | Tong et al. | |
| 10,741,778 B2 | 8/2020 | Kirsch et al. | |
| 11,063,227 B2* | 7/2021 | Kirsch | H01L 45/14 |
| 2005/0099209 A1 | 5/2005 | Luyken et al. | |
| 2006/0175604 A1* | 8/2006 | Ufert | G11C 13/0014 257/40 |
| 2008/0083921 A1* | 4/2008 | Yasue | H01L 51/005 257/E51.028 |
| 2009/0131384 A1 | 5/2009 | Uysal et al. | |
| 2010/0253997 A1 | 10/2010 | Li | |
| 2011/0140040 A1 | 6/2011 | Hattori et al. | |
| 2012/0105791 A1 | 5/2012 | Kornfield et al. | |
| 2014/0008601 A1 | 1/2014 | Nishizawa et al. | |
| 2014/0021438 A1 | 1/2014 | Hayashi et al. | |
| 2014/0138581 A1 | 5/2014 | Archetti et al. | |
| 2015/0105560 A1 | 4/2015 | Berny et al. | |
| 2015/0108421 A1 | 4/2015 | Hayashi et al. | |
| 2015/0115200 A1 | 4/2015 | Kawamura et al. | |
| 2015/0144198 A1 | 5/2015 | Irwin et al. | |
| 2016/0035496 A1 | 2/2016 | Irwin et al. | |
| 2016/0060530 A1 | 3/2016 | Archetti et al. | |
| 2017/0174990 A1 | 6/2017 | Rho et al. | |
| 2017/0253801 A1 | 9/2017 | Bae et al. | |
| 2017/0323929 A1 | 11/2017 | Bessonov et al. | |
| 2018/0006253 A1 | 1/2018 | Kirsch et al. | |
| 2018/0030020 A1 | 2/2018 | Reiffenrath et al. | |
| 2018/0258346 A1 | 9/2018 | Yun et al. | |
| 2021/0257569 A1* | 8/2021 | Kirsch ................ H01L 51/0073 | |

FOREIGN PATENT DOCUMENTS

| | | |
|---|---|---|
| CN | 103740376 A | 4/2014 |
| CN | 103773383 A | 5/2014 |
| DE | 10157674 A1 | 6/2002 |
| DE | 19927627 B4 | 1/2008 |
| DE | 102008006875 A1 | 8/2008 |
| DE | 102011108708 A1 | 3/2012 |
| DE | 102015002298 A1 | 9/2015 |
| DE | 102015000120 A1 | 7/2016 |
| EP | 0393462 B1 | 7/1995 |
| EP | 1394816 B1 | 3/2007 |
| EP | 1958999 B1 | 7/2012 |
| EP | 2380945 B1 | 5/2014 |
| EP | 2607451 B1 | 1/2019 |
| JP | 2002338690 A | 11/2002 |
| JP | 2005002164 A | 1/2005 |
| JP | 2006210922 A | 8/2006 |
| JP | 2007177051 A | 7/2007 |
| JP | 2008091930 A | 4/2008 |
| JP | 2009530399 A | 8/2009 |
| JP | 2011121909 A | 6/2011 |
| JP | 2014524951 A | 9/2014 |
| JP | 2015111737 A2 | 6/2015 |
| WO | 07111994 A2 | 10/2007 |
| WO | 12127542 A1 | 9/2012 |
| WO | 12127863 A1 | 9/2012 |
| WO | 13004372 A1 | 1/2013 |
| WO | 14169988 A1 | 10/2014 |
| WO | 17045740 A1 | 3/2017 |

OTHER PUBLICATIONS

Occhipinti et al., "Effectiveness and mode of action of phosphonate inhibitors of plant glutamine synthetase", Pest Management Science 2010, 66, 1, 51-58.

Ying-Zhe Chen et al., 'Construction of polyaromatics via photocyclization of 2-(fur-3-yl) ethenylarenes . . .', Tetrahedron, Elsevier Science Publishers, 2014, Bd. 70, Nr. 9, 1748-1762, XP028605962.

Fan Yang et al.: 'Structure-property relationship of naphthalene based donor-[pi]-acceptor organic dyes for dye-sensitized solar cells . . .', Journal of Materials Chemistry, 2012, Bd. 22, Nr. 42, 22550, XP055415006.

Office Action in corresponding JP 2019-500409 dated Jun. 30, 2021 (pp. 2-10).

European office action in corresponding EP 17739520.9 dated Jul. 17, 2020 (pp. 1-7).

International Search Report PCT/EP2017/066534 dated Jan. 4, 2018 (pp. 1-10).

Search report/ in corresponding SG 11201900082R dated May 15, 2020 (pp. 1-4 ).

Search report/Office Action in corresponding EP17739520.9 dated Mar. 18, 2020 (pp. 1-7).

Written opinion in corresponding SG 11201900082R dated May 15, 2020 (pp. 1-9 ).

* cited by examiner

ELECTRONIC SWITCHING ELEMENT

This application is a divisional of U.S. patent application Ser. No. 16/315,827, now U.S. Pat. No. 11,063,227.

The invention relates to an electronic switching element which contains a molecular layer of mesogenic compounds having negative dielectric anisotropy, and to electronic components based on this switching element. Further aspects of the invention relate to compounds for use in the molecular layer, to the use of the molecular layer and to processes for the production and operation of the electronic switching element and components based thereon.

In computer technology, storage media are required which allow rapid writing and reading access to information stored therein. Solid-state memories or semiconductor memories allow particularly fast and reliable storage media to be achieved, since absolutely no moving parts are necessary. At present, use is mainly made of dynamic random access memory (DRAM). DRAM allows rapid access to the stored information, but this information has to be refreshed regularly, meaning that the stored information is lost when the power supply is switched off.

The prior art also discloses non-volatile semiconductor memories, such as flash memory or magnetoresistive random access memory (MRAM), in which the information is retained even after the power supply has been switched off. A disadvantage of flash memory is that writing access takes place comparatively slowly and the memory cells of the flash memory cannot be erased ad infinitum. The lifetime of flash memory is typically limited to a maximum of one million read/write cycles. MRAM can be used in a similar way to DRAM and has a long lifetime, but this type of memory has not been able to establish itself owing to the difficult production process.

A further alternative is memory which works on the basis of memristors. The term memristor is a contraction of the words "memory" and "resistor" and denotes a component which is able to change its electrical resistance reproducibly between a high and a low electrical resistance. The respective state (high resistance or low resistance) is retained even without a supply voltage, meaning that non-volatile memories can be achieved with memristors.

An important alternative application of electrically switchable components arises for the area of neuromorphic or synaptic computing. In computer architectures pursued therein, the information is no longer intended to be processed sequentially in a classical manner. Instead, the aim is to build up the circuits in a highly three-dimensionally interlinked manner in order to be able to achieve information processing analogous to the brain. In artificial neuronal networks of this type, the biological connections between nerve cells (synapses) are then represented by the memristive switching elements. Under certain circumstances, additional intermediate states (between the digital states "1" and "0") may also be of particular benefit here.

WO 2012/127542 A1 and US 2014/008601 A1, for example, disclose organic molecular memories which have two electrodes and an active region which is arranged between the two electrodes. The active region has a molecular layer of electrically conductive aromatic alkynes, whose conductivity can be changed under the influence of an electric field. Similar components based on redox-active bipyridinium compounds are proposed in US 2005/0099209 A1.

The known memories based on a change in conductivity or resistance have the disadvantage that the free-radical intermediates formed by the flow of current through the molecules of the monolayer are in principle susceptible to degradation processes, which has an adverse effect on the lifetime of the components.

The object was therefore to search for novel electronic components which are suitable for use in memristive devices and bring improvements, in particular, with respect to one or more of the following properties:

the selectability and readability of two states ("0", "1") which are sufficiently different with respect to their electrical resistance, with the aid of an electric field or current;

the switching voltage should be in the range from a few 100 mV to a few V;

the reading voltage should be significantly lower than the writing voltage (typical ratio 1:10 [V]);

the reading current should be at least 100 nA in state "1";

the resistance ratio between the high resistance state (HRS) (corresponds to "0") and the low resistance state (LRS) (corresponds to "1"): $R_{HRS}$:$R_{LRS}$ should be 10 or more, the resistance ratio should particularly preferably be 1000 or more;

the access times for the writing and reading operation should be 100 ns or less;

the long-term stability of the selected states at room temperature without the need to periodically refresh them and thus maintain a continuous power supply should be greater than 10 years, even in the case of continuous reading;

a broad temperature range for operation and storage while maintaining the stored information is desirable;

a high degree of reversibility of the switching operation without "fatigue phenomena" ($>1.0 \cdot 10^6$ switching cycles) is desirable ("endurance");

the potential for high integration densities down to the molecular size scale (<10 nm) should exist;

compatibility with standard methods, processes, switching parameters and design rules of silicon electronics (CMOS) should be possible;

simple and thus inexpensive device architecture should be possible.

It has now been found that these objects can be achieved, at least in partareas, if the switching elements of corresponding components contain a molecular layer comprising mesogenic compounds having negative dielectric anisotropy, which are fixed by reaction of the surface of the switching element with a terminal double bond of the mesogenic compounds or which are fixed by interaction of the surface with a terminal polar anchor group of the mesogenic compounds.

Mesogenic compounds having negative dielectric anisotropy, including those which contain a terminal double bond in a side chain, are known to the person skilled in the art. Thus, for example, DE 199 27 627 B4 discloses the following compound:

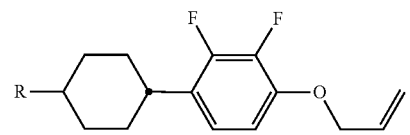

in which R denotes, inter alia, an alkyl radical.

A related compound is known from DE 10 2008 006875 A1:

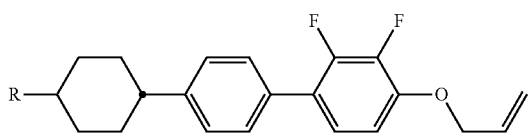

in which R denotes, inter alia, an alkyl radical.

DE 10157674 A1 discloses the following compound:

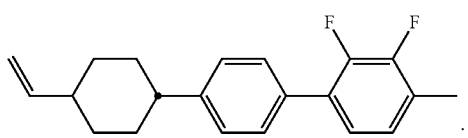

A further class of liquid crystals having negative dielectric anisotropy is formed, for example, by the difluorodibenzofurans of the structure shown below, which are disclosed in DE 10 2015 002298 A1, in which compounds having a terminal C—C double bond are likewise described:

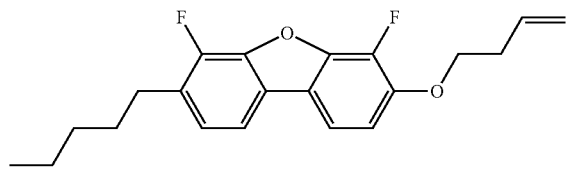 [SMILES: C=CCCOc1ccc2c(oc3c(F)c(CCCCC)ccc32)c1F]

Mesogenic compounds containing a terminal polar anchor group are likewise known in principle from the prior art. JP 2007 177051 A describes mesogenic compounds having positive dielectric anisotropy which are proposed for the derivatisation of iron oxide nanoparticles; the bonding to the particles takes place here through phosphate, phosphonate or carboxylate groups located at the end of the side chain. WO 2013/004372 A1 and WO 2014/169988 A1 disclose mesogenic compounds which carry terminal hydroxyl groups and serve for the derivatisation of substrates for liquid-crystal displays with the aim of homeotropic alignment of the liquid crystal. A corresponding use of dielectrically neutral and positive mesogenic compounds containing polar anchor groups is disclosed in JP2005/002164 A.

Angew. Chem. Int. Ed. 51 (2012), 4658 (H. J. Yoon et al.) and J. Am. Chem. Soc. 136 (2014) 16-19 (H. J. Yoon et al.) describe arrangements in which the electronic potential is measured over monolayers of alkyl compounds containing polar end groups. Suitability of such layers for use in switching elements of memristive electronic components cannot be derived therefrom; mesogenic compounds or compounds having negative dielectric anisotropy are neither mentioned therein, nor is their suitability suggested.

The invention therefore relates to an electronic switching element which comprises, in this sequence,
a first electrode,
a molecular layer bonded to a substrate, and
a second electrode,
where the molecular layer essentially consists of one or more compounds of the formula I:

in which
$R^1$ denotes H, an alkyl or alkoxy radical having 1 to 15 C atoms, where, in addition, one or more $CH_2$ groups in these radicals may each be replaced, independently of one another, by —C≡C—, —CH═CH—,

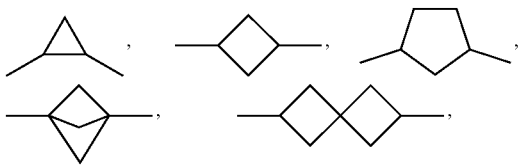

—O—, —S—, —CF$_2$O—, —OCF$_2$—, —CO—O—, or —O—CO—, —SiR$^O$R$^{OO}$—, —NH—, —NR$^O$— or —SO$_2$— in such a way that O atoms are not linked directly to one another, and in which, in addition, one or more H atoms may be replaced by halogen, CN, SCN or SF$_5$, $R^O$, $R^{OO}$, identically or differently, denote an alkyl or alkoxy radical having 1 to 15 C atoms, in which, in addition, one or more H atoms may be replaced by halogen, $A^1$, $A^2$ on each occurrence, identically or differently, denote an aromatic, heteroaromatic, alicyclic or heteroaliphatic ring having 4 to 25 ring atoms, which may also contain condensed rings and which may be mono- or polysubstituted by Y'

Y on each occurrence, identically or differently, denotes F, Cl, CN, SCN, SF$_5$ or straight-chain or branched, in each case optionally fluorinated alkyl, alkoxy, alkylcarbonyl, alkoxycarbonyl, alkylcarbonyloxy or alkoxycarbonyloxy having 1 to 12 C atoms, preferably F or Cl, $B^1$
denotes

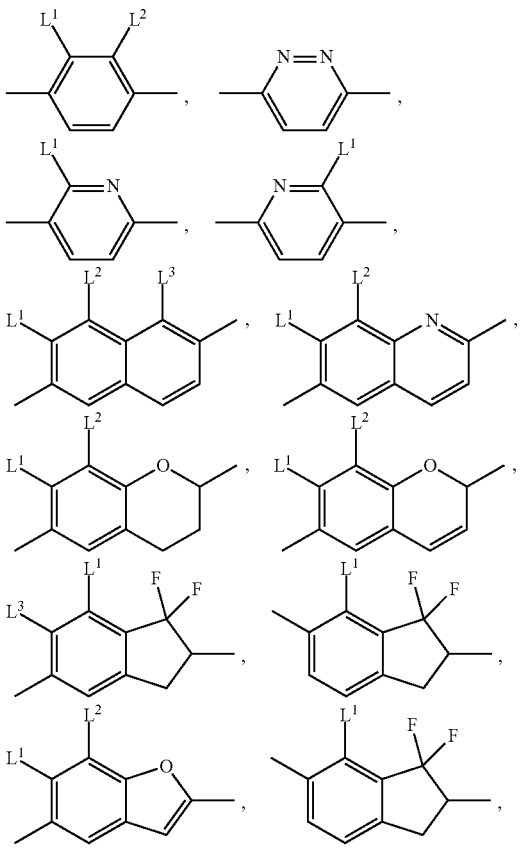

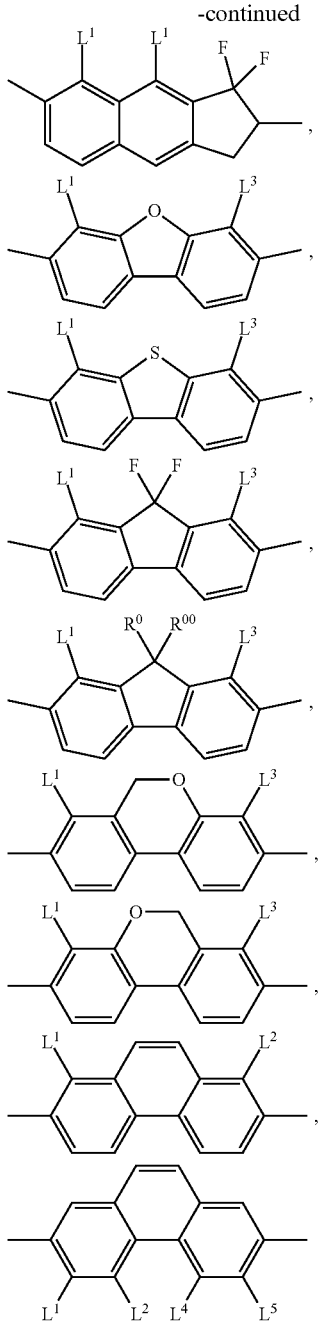

where the groups may be oriented in both directions, $L^1$ to $L^5$, independently of one another, denote F, Cl, Br, I, CN, $SF_5$, $CF_3$ or $OCF_3$, preferably Cl or F, where $L^3$ may alternatively also denote H, $Z^1$, $Z^2$ on each occurrence, identically or differently, denote a single bond, —$CF_2O$—, —$OCF_2$—, —$CF_2S$—, —$SCF_2$—, —$CH_2O$—, —$OCH_2$—, —C(O)O—, —OC(O)—, —C(O)S—, —SC(O)—, —$CH_2$—, —$(CH_2)_2$—, —$(CH_2)_3$—, —$(CH_2)_4$—, —$CF_2$—, —$CF_2$—$CF_2$—, —$CF_2$—$CH_2$—, —$CH_2$—$CF_2$—, —CH=CH—, —CF=CF—, —CF=CH—, —CH=CF—, —$(CH_2)_3O$—, —$O(CH_2)_3$—, —C≡C—, —O—, —S—, —C=N—, —N=C—, —N=N—, —N=N(O)—, —N(O)=N— or —N=C—C=N—, Sp denotes a spacer group or a single bond, G denotes —CH=$CH_2$, —OH, —SH, —$SO_2OH$, —OP(O)(OH)$_2$, —PO(OH)$_2$, —C(OH)(PO(OH)$_2$)$_2$, —COOH, —Si(OR$^x$)$_3$ or —SiCl$_3$, $R^x$ denotes straight-chain or branched alkyl having 1 to 6 C atoms, and r and s, independently of one another, denote 0, 1, 2 or 3, where r+s≤4.

The switching elements are set up, in particular, to change between a state having high electrical resistance and a state having low electrical resistance, where the quotient between high electrical resistance and low electrical resistance is preferably between 10 and 100,000. The electrical resistance is measured by applying a reading voltage to the switching element and measuring the electric current flowing through the switching element. The change between the states takes place by application of a switching voltage. The value of the reading voltage is lower than the value of the switching voltage, where the value of the reading voltage is preferably a maximum of one tenth of the value of the smallest switching voltage used. It is particularly preferred if the reading voltage is from 10 to 300 mV.

The invention furthermore relates to an electronic component comprising a plurality of switching elements according to the invention, such as, for example, a memristive component, in particular one which has been designed as a crossbar array.

The invention furthermore relates to a process for the production of the switching element according to the invention comprising at least the following steps:
i. production of a first electrode (20)
ii. deposition of a monolayer (18) comprising one or more compounds of the formula I
iii. application of a second electrode (16).

The deposition of the monolayer is carried out with the aid of the pure substance or from solution, preferably from solution. Suitable deposition methods and solvents are known to the person skilled in the art; examples are spin coating or dip coating.

In a preferred embodiment, the substrate is annealed after deposition of the monolayer. The annealing is carried out at a temperature of greater than 20° C. and less than 300° C., preferably at greater than 50° C. and less than 200° C., particularly preferably at greater than 90° C. and less than 150° C. The time duration of the annealing is 1 to 48 h, preferably 4 to 24 h, particularly preferably 8 to 16 h.

The production and structuring of the electrodes is carried out by means of processes known to the person skilled in the art and is explained in greater detail below with reference to the working examples.

The invention furthermore relates to a method for operating the electronic component according to the invention, characterised in that a switching element of the electronic component is switched into a state of high electrical resistance by setting a corresponding first electrode to a first electrical potential and setting a corresponding second electrode to a second electrical potential, where the value of the voltage between the two electrodes is greater than a first switching voltage and the first potential is greater than the second potential, a switching element of the electronic component is switched into a state of low electrical resistance by setting a corresponding first electrode to a third electrical potential and setting a corresponding second electrode to a fourth electrical potential, where the value of the voltage between the two electrodes is greater than a second switching voltage and the fourth potential is greater than the third potential, and the state of a switching element is determined by applying a reading voltage whose value is smaller than the first and second switching voltages between corresponding electrodes and measuring the current flowing.

The invention likewise relates to the use of switching elements according to the invention in a memristive electronic component.

The invention furthermore relates to the use of compounds of the formula I as molecular layer in switching elements of a memristive electronic component.

The invention furthermore relates to compounds of the formula I as indicated above in which G denotes —OH, —SH, —SO$_2$OH, —OP(O)(OH)$_2$, —P(O)(OH)$_2$, —C(OH)(PO(OH)$_2$)$_2$, —COOH, —Si(OR$^x$)$_3$ or —SiCl$_3$, preferably —OP(O)(OH)$_2$, —P(O)(OH)$_2$, or —C(OH)(P(O)(OH)$_2$)$_2$, and the other substituents and parameters have the meanings indicated above under formula I.

The invention furthermore relates, in particular, to compounds of the formula I as indicated above in which Sp denotes —O(CF$_2$)$_{p1}$— or —(CF$_2$)$_{p1}$— and p1 denotes an integer from 1 to 12 and the other substituents and parameters have the meanings indicated above.

Figure 1:
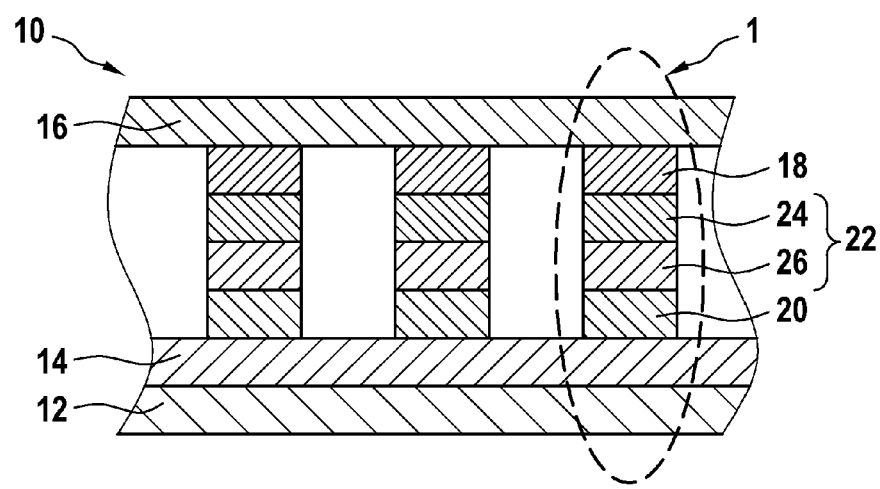
FIG. 1 shows a first embodiment of an electronic component.

The switching elements according to the invention are suitable for use in electronic components, in particular memristive components, which exhibit the advantageous properties indicated above.

The term "mesogenic group" is known to the person skilled in the art and is defined in accordance with C. Tschierske, G. Pelzl, S. Diele, Angew. Chem. 2004, 116, 6340-6368, as the part of a molecule or macromolecule which, due to the anisotropy of its attracting and repelling interactions, makes a significant contribution to the low-molecular-weight or polymeric substances forming a liquid-crystalline mesophase. The majority of mesogenic groups consist of rigid rod- or disc-shaped units.

A mesogenic compound ("mesogen" for short) is characterised in that it contains one or more mesogenic groups. The mesogenic compounds here do not necessarily have to have a liquid-crystalline phase themselves.

The dielectric anisotropy $\Delta\varepsilon$ of a uniaxial mesogenic compound is defined as the difference between the dielectric constants parallel ($\varepsilon_\parallel$) and perpendicular ($\varepsilon_\perp$) to the longitudinal axis of the molecule. In the case of dielectrically negative compounds, it follows that $\Delta\varepsilon=(\varepsilon_\parallel-\varepsilon_\perp)<0$.

An anchor group in the sense of the present invention is a functional group by means of which the mesogenic compound is adsorbed onto or bonded to the surface of the substrate by physisorption, chemisorption or by chemical reaction.

A spacer group in the sense of the present invention is a flexible chain between mesogenic group and anchor group which causes a separation between these sub-structures and, owing to its flexibility, at the same time improves the mobility of the mesogenic group after bonding to a substrate.

If $R^1$ represents an alkyl radical, this is straight-chain or branched and has 1 to 15 C atoms. $R^1$ is preferably straight-chain and has, unless indicated otherwise, 1, 2, 3, 4, 5, 6 or 7 C atoms and is accordingly preferably methyl, ethyl, propyl, butyl, pentyl, hexyl or heptyl.

If $R^1$ represents an alkoxy radical, this is straight-chain or branched and contains 1 to 15 C atoms. $R^1$ is preferably straight-chain and has, unless indicated otherwise, 1, 2, 3, 4, 5, 6 or 7 C atoms and is accordingly preferably methoxy, ethoxy, propoxy, butoxy, pentoxy, hexoxy or heptoxy.

$R^1$ in formula I can furthermore be an alkenyl radical having 2 to 15 C atoms, which is straight-chain or branched and contains at least one C—C double bond. It is preferably straight-chain and has 2 to 7 C atoms. Accordingly, it is preferably vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl. If the two C atoms of the C—C double bond are substituted, the alkenyl radical can be in the form of E and/or Z isomer (trans/cis). In general, the respective E isomers are preferred. Of the alkenyl radicals, prop-2-enyl, but-2- and -3-enyl, and pent-3- and -4-enyl are particularly preferred. $R^1$ in formula I can also be an alkynyl radical having 2 to 15 C atoms, which is straight-chain or branched and contains at least one C—C triple bond. 1- and 2-propynyl and 1-, 2- and 3-butynyl are preferred.

Preferred aryl groups are derived, for example, from the parent structures benzene, naphthalene, tetrahydronaphthalene, 9,10-dihydrophenanthrene, fluorene, indene and indane.

Preferred heteroaryl groups are, for example, five-membered rings furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole and 1,3,4-thiadiazole, six-membered rings, such as, for example, pyridine, pyridazine, pyrimidine, pyrazine, 1,3,5-triazine, 1,2,4-triazine and 1,2,3-triazine, or condensed rings, such as, for example, indole, isoindole, indolizine, indazole, benzimidazole, benzotriazole, purine, naphthimidazole, benzoxazole, naphthoxazole, benzothiazole, benzofuran, isobenzofuran, dibenzofuran, thieno[2,3b]thiophene, thieno[3,2b]thiophene, dithienothiophene, isobenzothiophene, dibenzothiophene, benzothiadiazothiophene, 2H-chromen (2H1-benzopyran), 4H-chromene (4H-1-benzopyran) and coumarin (2H-chromen-2-one), or combinations of these groups.

Preferred cycloaliphatic groups are cyclobutane, cyclopentane, cyclohexane, cyclohexene, cycloheptane, decahydronaphthalene, bicyclo[1.1.1]pentane, bicyclo[2.2.2]octane, spiro[3.3]heptane and octahydro-4,7-methanoindane.

Preferred heteroaliphatic groups are tetrahydrofuran, dioxolane, tetrahydrothiofuran, pyran, dioxane, dithiane, silinane, piperidine and pyrrolidine.

$A^1$ and $A^2$, independently of one another and identically or differently on each occurrence, are particularly preferably selected from the following groups:
 a) 1,4-phenylene, in which, in addition, one or two CH groups may be replaced by N and in which, in addition, one or more H atoms may be replaced by Y,
 b) the group consisting of trans-1,4-cyclohexylene and 1,4-cyclohexenylene, in which, in addition, one or more non-adjacent $CH_2$ groups may be replaced by —O— and/or —S— and in which, in addition, one or more H atoms may be replaced by Y, and
 c) the group consisting of 1,3-dioxolane-2,4-diyl, tetrahydrofuran-2,5-diyl, cylcobutane-1,3-diyl, 1,4-bicyclo[2.2.2]octanediyl, piperidine-1,5-diyl and thiophene-2,5-diyl, which, in addition, may be replaced one or more times by Y, where Y has the meaning indicated above under formula I and preferably denotes F, Cl, CN or $CF_3$.

In formula I, Sp preferably denotes a spacer group.

Preferred spacer groups Sp are selected from the formula Sp'—X'—, so that the radical G-Sp— corresponds to the formula G-Sp'—X'—, where Sp' denotes straight-chain or branched alkylene having 1 to 20, preferably 1 to 12 C atoms, which is optionally mono- or polysubstituted by F, Cl, Br, I or CN and in which, in addition, one or more non-adjacent $CH_2$ groups may each be replaced, independently of one another, by —O—, —S—, —NH—, —NR$^o$—, —SiR$^{oo}$R$^{ooo}$—, —CO—, —COO—, —OCO—, —OCO—O—, —S—CO—, —CO—S—, —NR$^{oo}$—CO—O—, —O—CO—NR$^{oo}$—, —NR$^{oo}$—CO—NR$^{oo}$—, —CH=CH— or —C≡C— in such a way that O and/or S atoms are not linked directly to one another, X' denotes —O—, —S—, —CO—, —COO—, —OCO—, —O—COO—, —CO—NR$^{oo}$—, —NR$^{oo}$—CO—, —NR$^{oo}$—CO—NR$^{oo}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^{oo}$—, —CY$^x$=CY$^{x'}$—, —C≡C—, —CH=CH—COO—, —OCO—CH=CH— or a single bond, $R^o$ and $R^{oo}$ each, independently of one another, denote H or alkyl having 1 to 12 C atoms, and $Y^x$ and $Y^{x'}$ each, independently of one another, denote H, F, Cl or CN.

X' is preferably —O—, —S—CO—, —COO—, —OCO—, —O—COO—, —CO—NR$^o$—, —NR$^o$—CO—, —NR$^o$—CO—NR$^o$— or a single bond.

Typical spacer groups Sp' are, for example, —(CH$_2$)$_{p1}$—, —(CF$_2$)$_{p1}$—, —(CH$_2$CH$_2$O)$_{q1}$—CH$_2$CH$_2$—, —(CF$_2$CF$_2$O)$_{q1}$—CF$_2$CF$_2$—, —CH$_2$CH$_2$—S—CH$_2$CH$_2$—, —CH$_2$CH$_2$—NH—CH$_2$CH$_2$— or —(SiR$^{oo}$R$^{ooo}$—O)$_{p1}$—, in which p1 is an integer from 1 to 12, q1 is an integer from 1 to 3, and $R^{oo}$ and $R^{ooo}$ have the meanings indicated above.

Particularly preferred groups —X'—Sp'— are —(CH$_2$)$_{p1}$—, —O—(CH$_2$)$_{p1}$—, —(CF$_2$)$_{p1}$—, —O(CF$_2$)$_{p1}$—, —OCO—(CH$_2$)$_{p1}$— and —OC(O)O—(CH$_2$)$_{p1}$—, in which p1 has the meaning indicated above.

Particularly preferred groups Sp' are, for example, in each case straight-chain ethylene, propylene, butylene, pentylene, hexylene, heptylene, octylene, nonylene, decylene, undecylene, dodecylene, octadecylene, perfluoroethylene, perfluoropropylene, perfluorobutylene, perfluoropentylene, perfluorohexylene, perfluoroheptylene, perfluorooctylene, perfluorononylene, perfluorodecylene, perfluoroundecylene, perfluorododecylene, perfluorooctadecylene, ethyleneoxyethylene, methyleneeoxybutylene, ethylenethioethylene, ethylene-N-methyliminoethylene, 1-methylalkylene, ethenylene, propenylene and butenylene.

Particularly preferred sub-formulae of the formula I are the sub-formulae Ia to If shown below:

| | |
|---|---|
| $R^1$—$B^1$-Sp-G | Ia |
| $R^1$-($A^1$-$Z^1$)—$B^1$-Sp-G | Ib |
| $R^1$-($A^1$-$Z^1$)$_2$—$B^1$-Sp-G | Ic |
| $R^1$—$B^1$—(—$Z^2$-$A^2$)-Sp-G | Id |
| $R^1$—$B^1$—($Z^2$-$A^2$)$_2$-Sp-G | Ie |
| $R^1$-($A^1$-$Z^1$)—$B^1$—($Z^2$-$A^2$-)-Sp-G | If | in which $R^1$, $A^1$, $A^2$, $B^1$, $Z^1$, $Z^2$, Sp and G have the meanings indicated above and preferably $A^1$ and $A^2$ denote

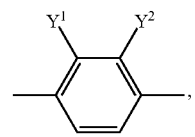 , 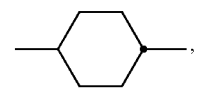 , $B^1$ denotes

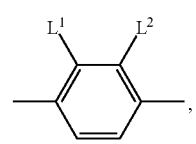 , 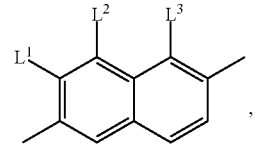 ,

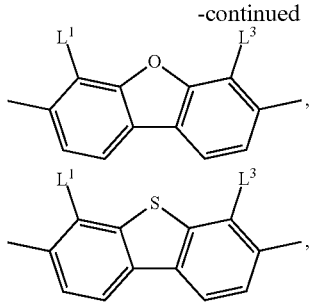

where the groups may be oriented in both directions,

R¹ denotes alkyl having 1-15 C atoms, preferably having 1-7 C atoms, in particular $CH_3$, $C_2H_5$, $n-C_3H_7$, $n-C_4H_9$, $n-C_5H_{11}$, $n-C_6H_{13}$ or $n-C_7H_{15}$.

L¹ and L², independently of one another, denote Cl or F, where at least one of the radicals L¹ and L² denotes F, L³ denotes F, Y¹ and Y², independently of one another, denote H, Cl or F, Z¹, Z², independently of one another, denote a single bond, —CF₂O—, —OCF₂—, —CH₂O—, OCH₂— or —CH₂CH₂—, Sp denotes unbranched 1,ω-alkylene having 1 to 12 C atoms, G denotes —CH═CH₂, —OH, —SH, —SO₂OH, —OP(O)(OH)₂, —PO(OH)₂, —COH(PO(OH)₂)₂, —COOH, —Si(OR)₃ or —SiCl₃.

In a further preferred embodiment, in the compounds of the formulae Ia to If,

Sp denotes unbranched 1,ω-perfluoroalkylene having 1 to 12 C atoms, where R¹, A¹, A², B¹, Z¹, Z² and G have the meanings indicated above.

Very particularly preferred sub-formulae of the formula I are the sub-formulae Ia, Ib and Id.

Examples of preferred compounds of the formulae Ia to If are shown below:

Ia-1
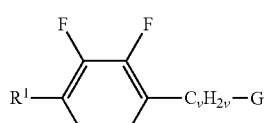

Ia-2
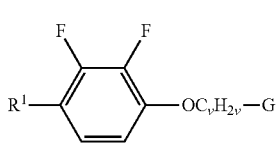

Ia-3
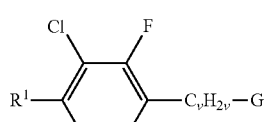

Ia-4
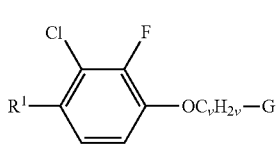

Ia-5
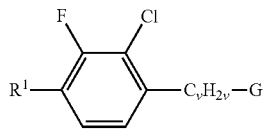

Ia-6
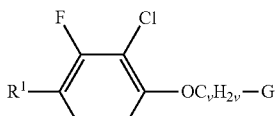

Ia-7
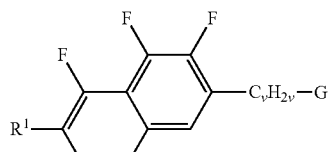

Ia-8
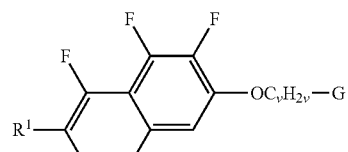

Ia-9
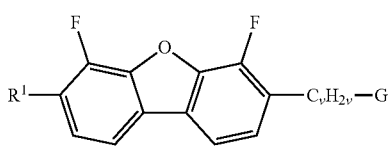

Ia-10
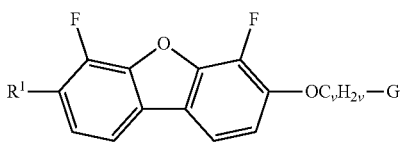

Ia-11
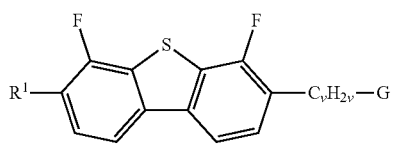

Ia-12
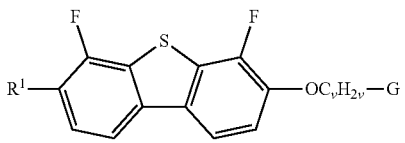

Ib-1
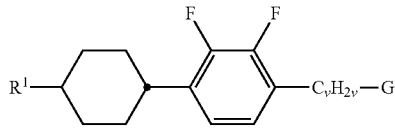

Ib-2
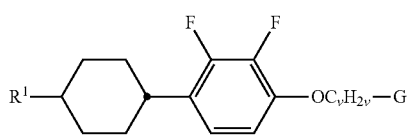

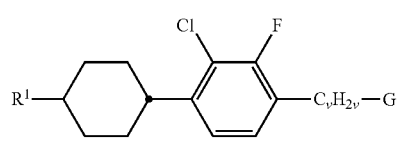 Ib-3
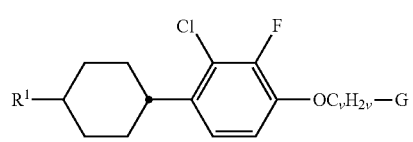 Ib-4
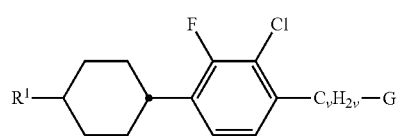 Ib-5
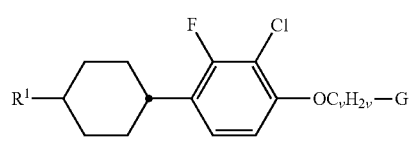 Ib-6
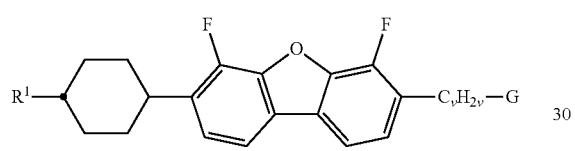 Ib-7
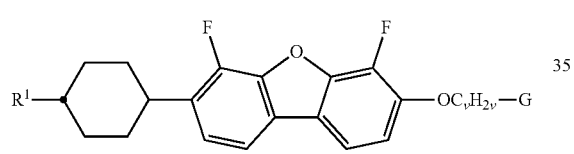 Ib-8
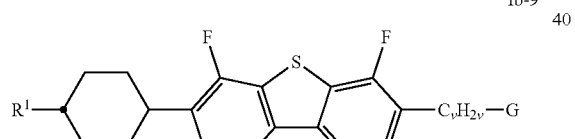 Ib-9
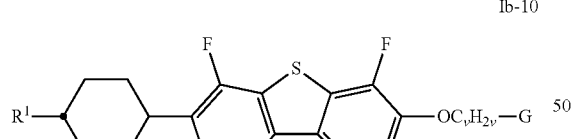 Ib-10
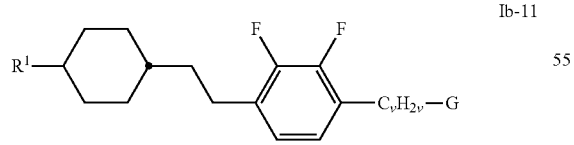 Ib-11
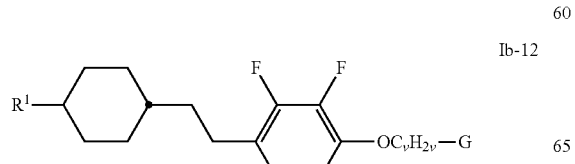 Ib-12
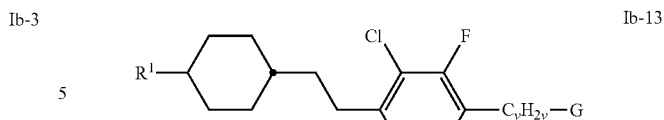 Ib-13
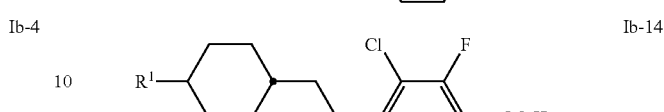 Ib-14
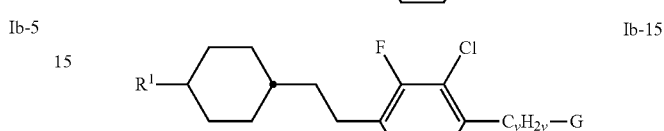 Ib-15
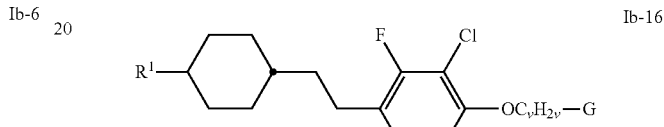 Ib-16
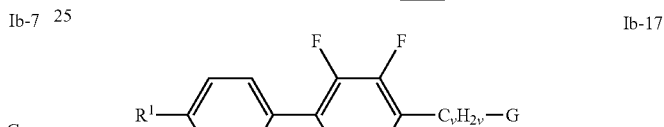 Ib-17
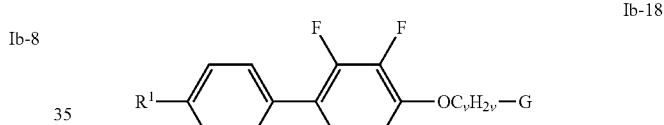 Ib-18
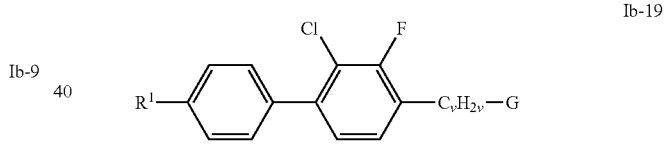 Ib-19
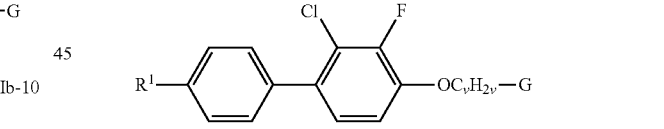 Ib-20
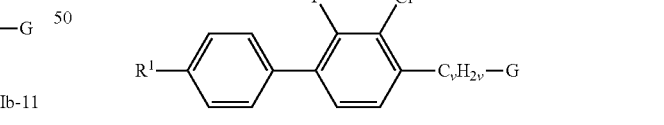 Ib-21
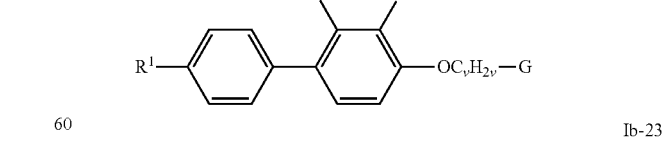 Ib-22
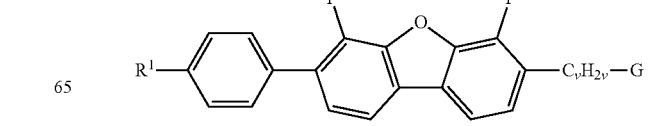 Ib-23

Ib-24
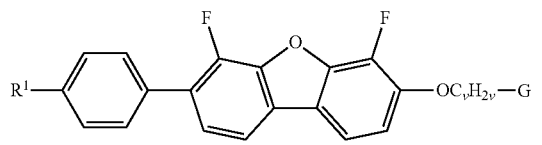
Ib-25
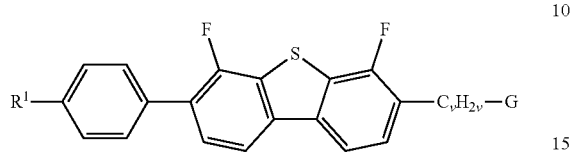
Ib-26
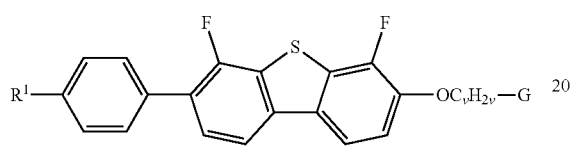
Ib-27
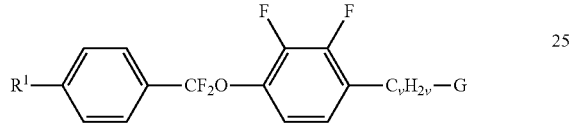
Ib-28
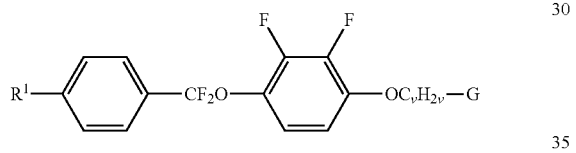
Ib-29
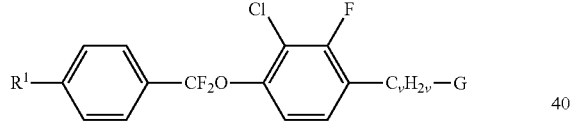
Ib-30
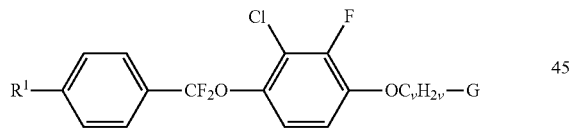
Ib-31
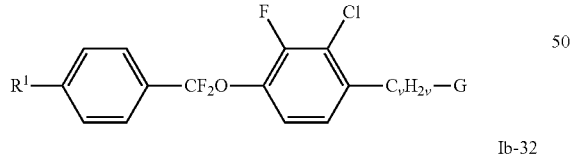
Ib-32
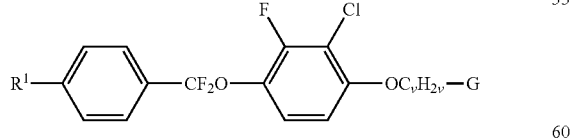
Ic-1
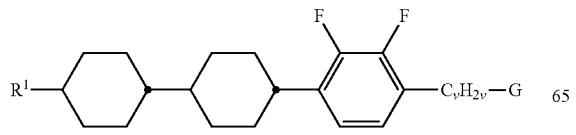
Ic-2
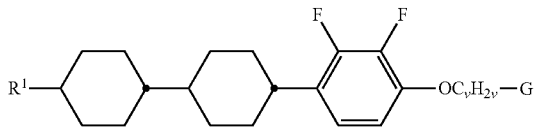
Ic-3
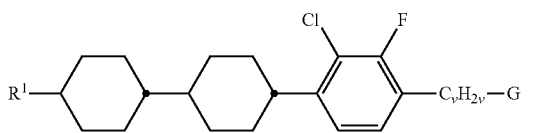
Ic-4
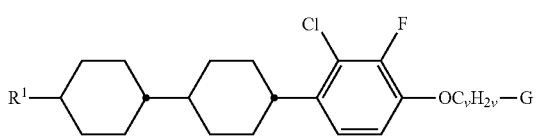
Ic-5
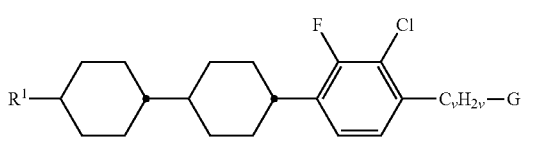
Ic-6
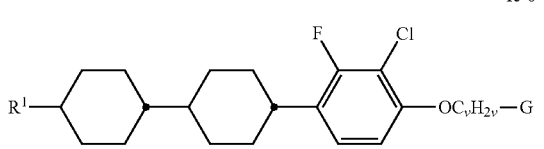
Ic-7
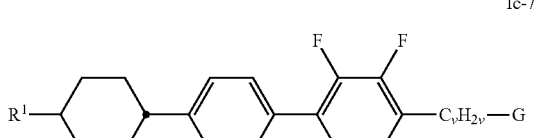
Ic-8
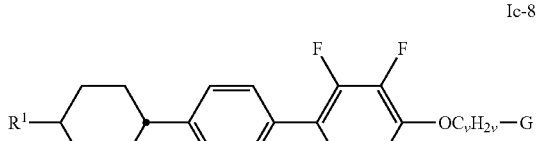
Ic-9
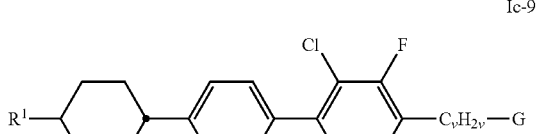
Ic-10
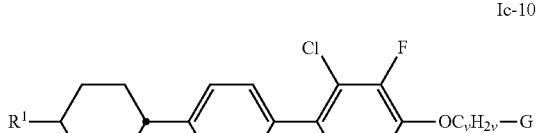
Ic-11
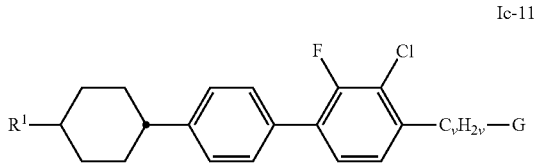

Ic-12
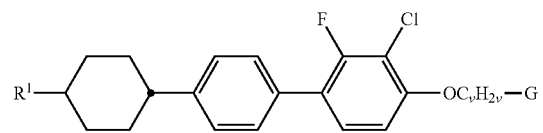
Ic-13
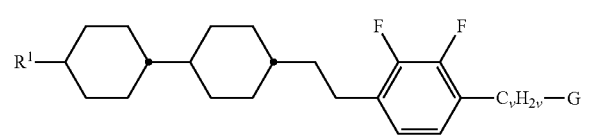
Ic-14
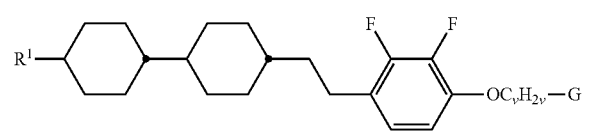
Ic-15
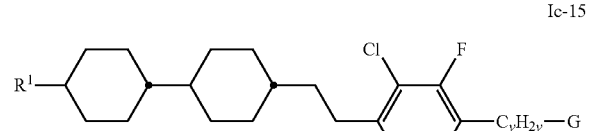
Ic-16
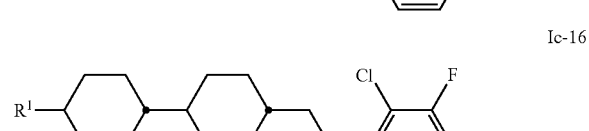
Ic-17
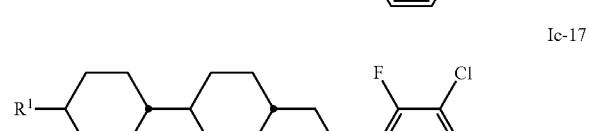
Ic-18
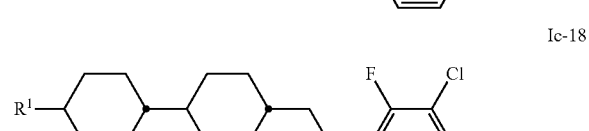
Ic-19
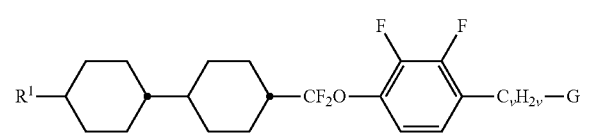
Ic-20
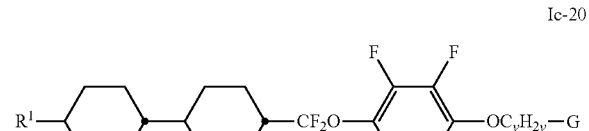
Ic-21
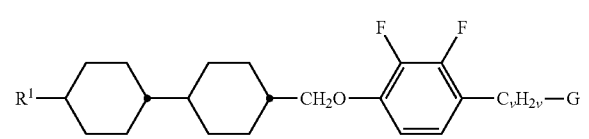
Ic-22
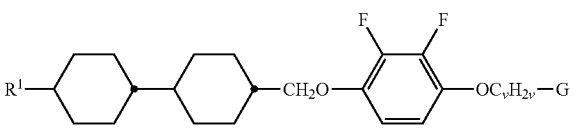
Ic-23
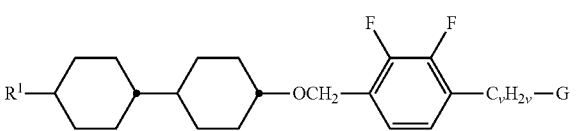
Ic-24
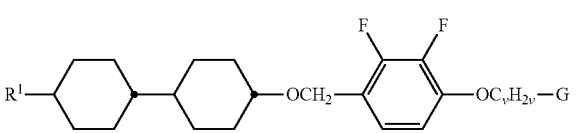
Ic-25
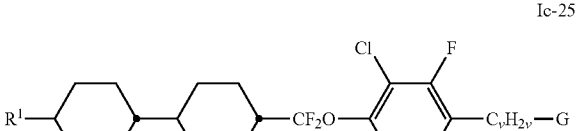
Ic-26
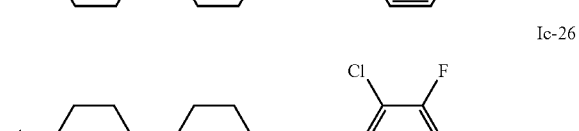
Ic-27
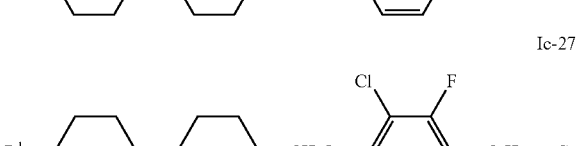
Ic-28
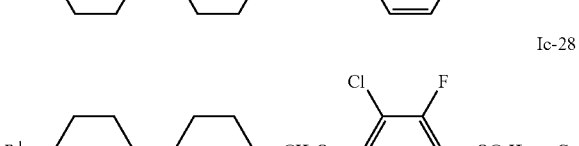
Ic-29
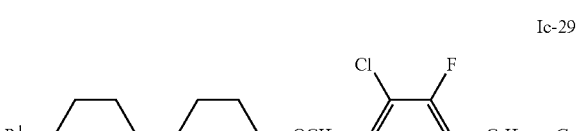
Ic-30
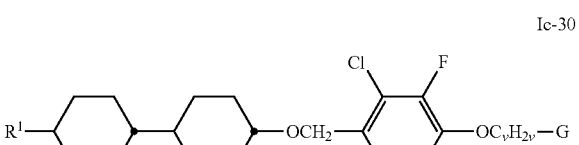
Ic-31
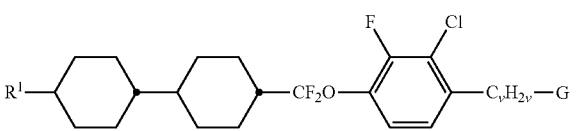

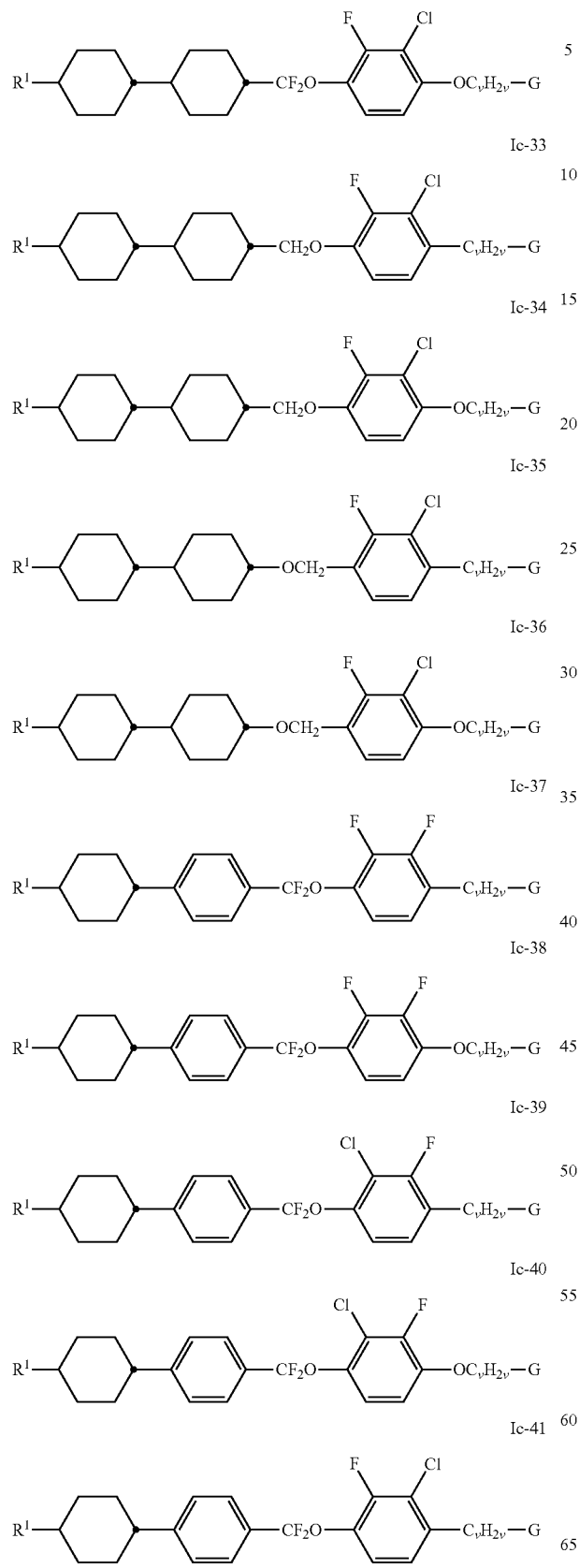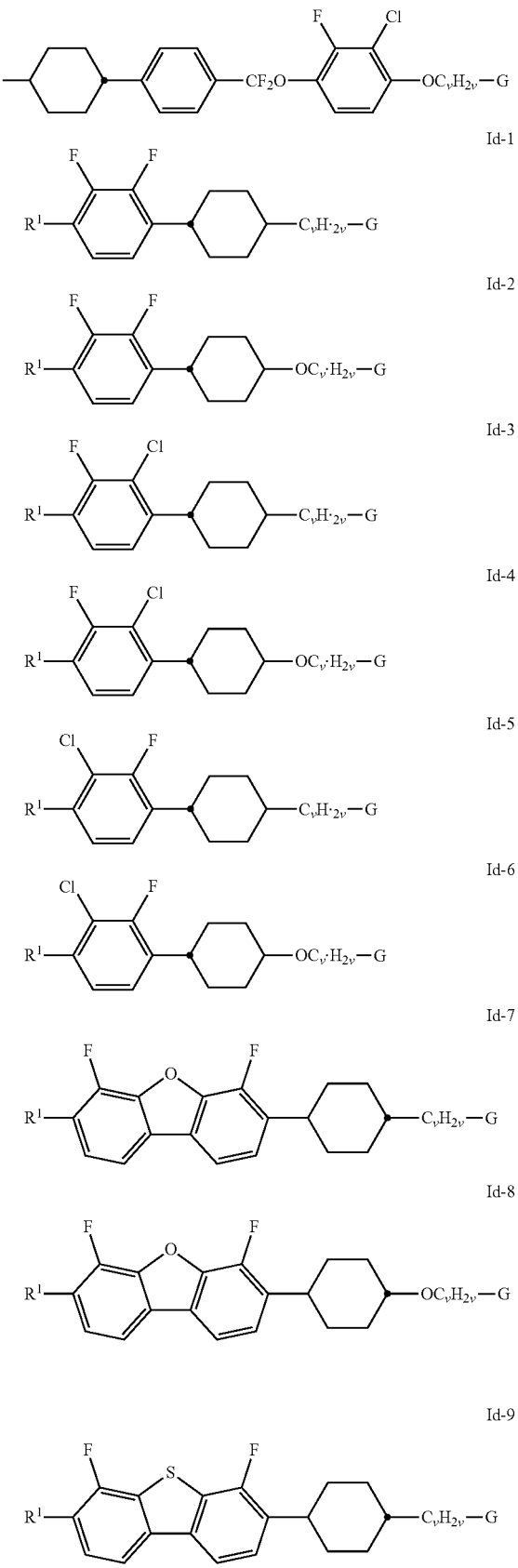

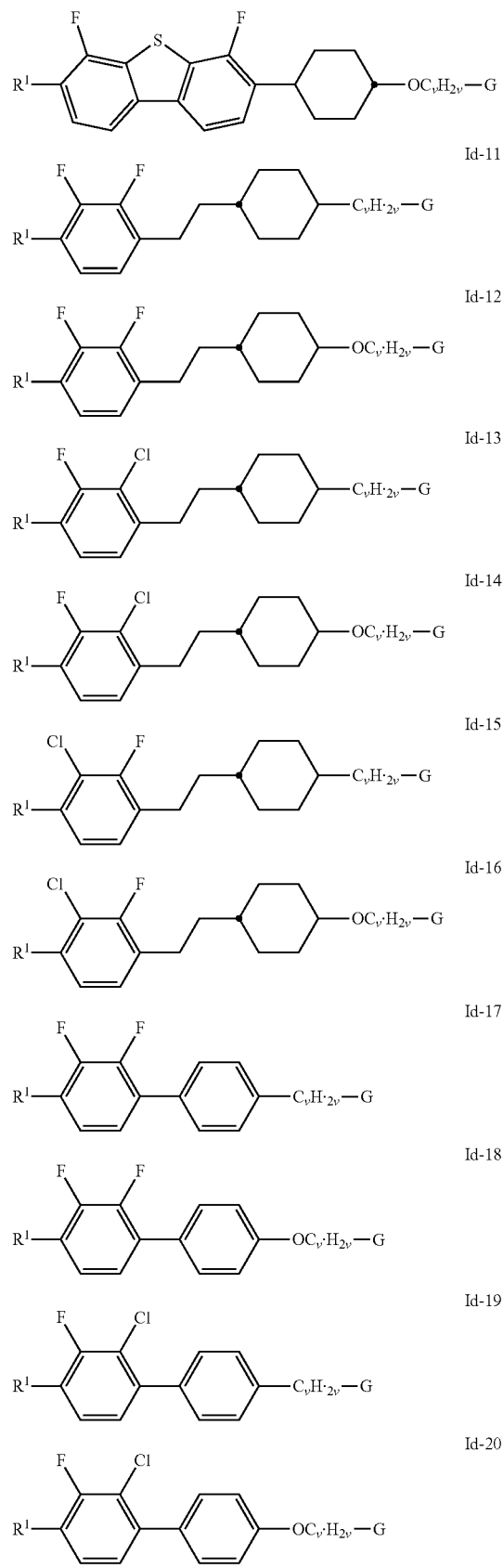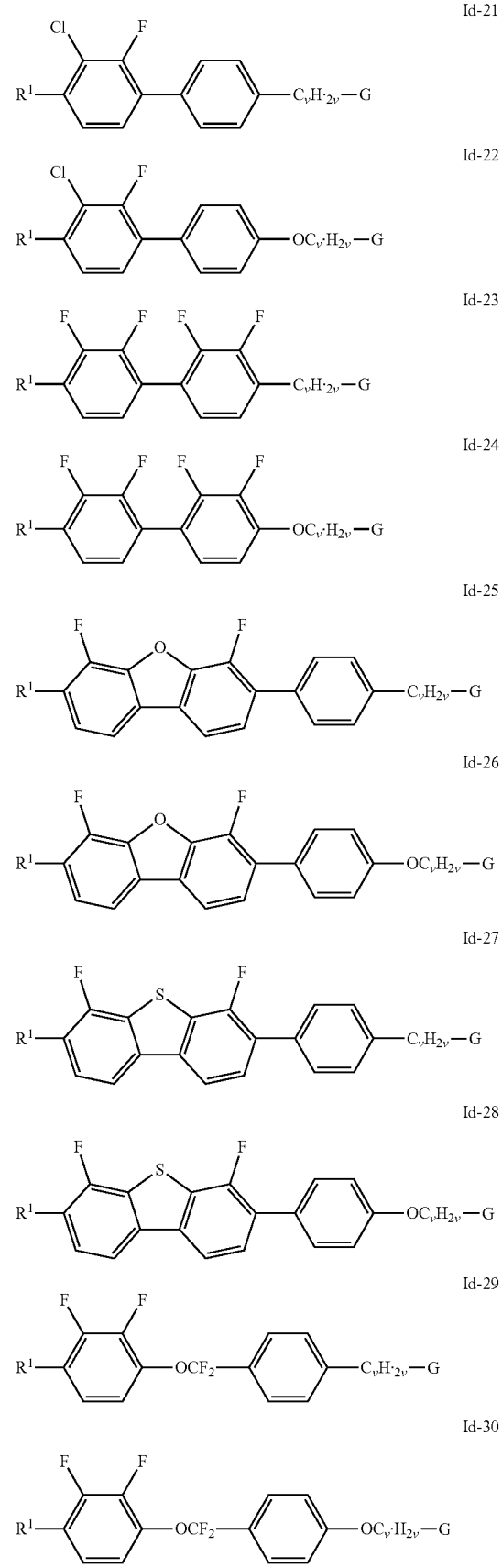

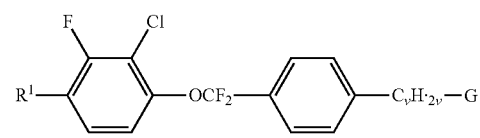
Id-31
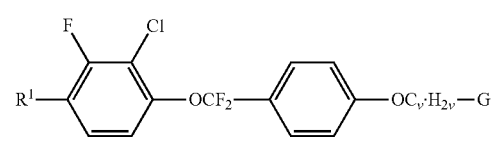
Id-32
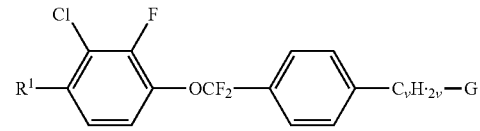
Id-33
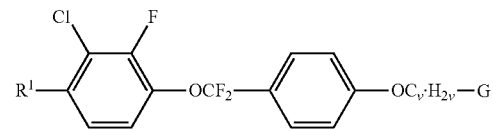
Id-34
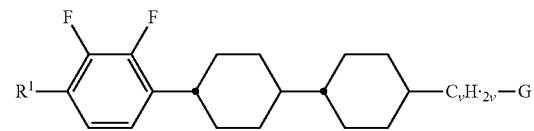
Ie-1
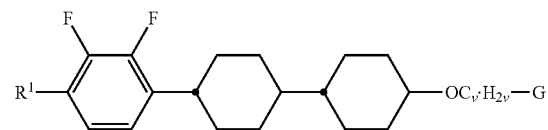
Ie-2
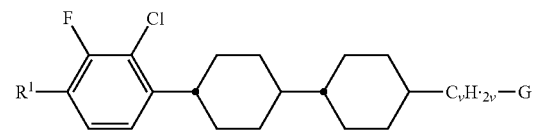
Ie-3
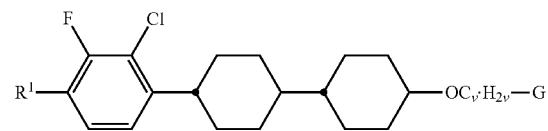
Ie-4
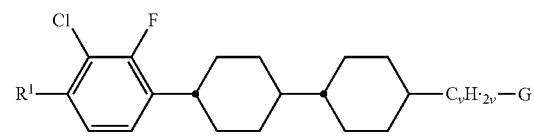
Ie-5
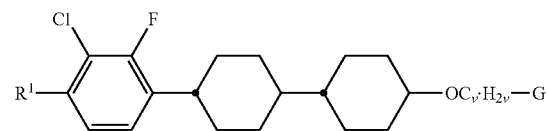
Ie-6
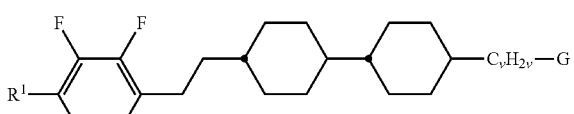
Ie-7
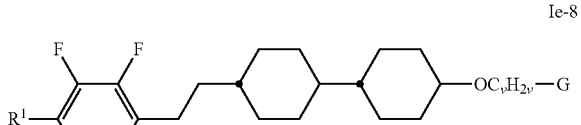
Ie-8
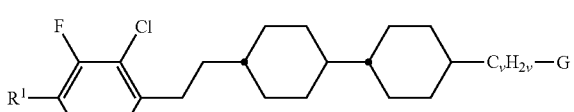
Ie-9
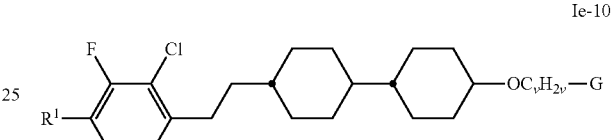
Ie-10
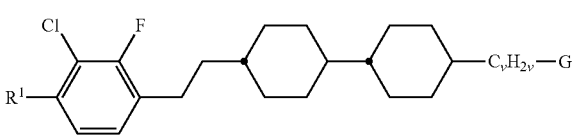
Ie-11
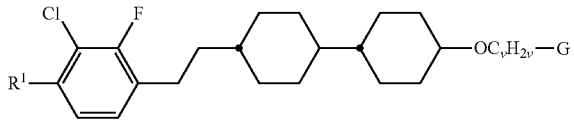
Ie-12
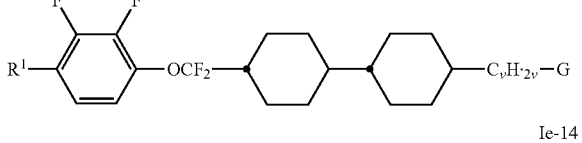
Ie-13
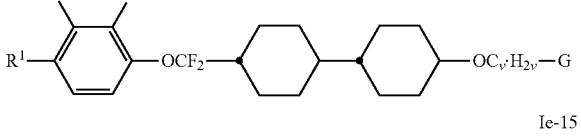
Ie-14
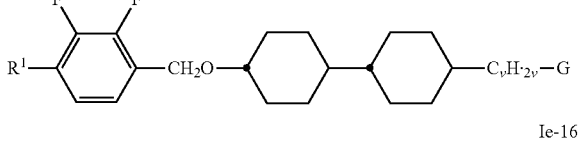
Ie-15
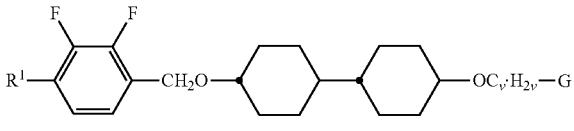
Ie-16

Ie-17
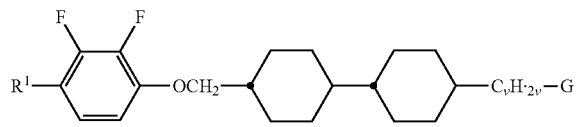
Ie-18
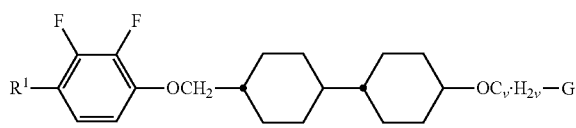
Ie-19
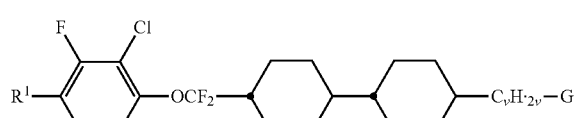
Ie-20
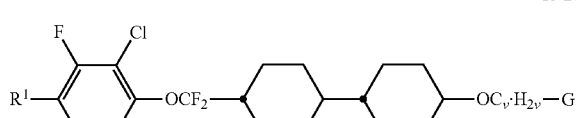
Ie-21
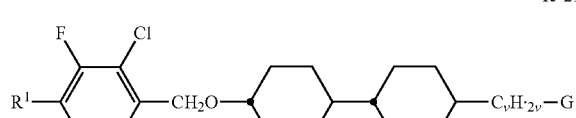
Ie-22
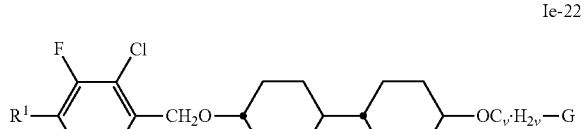
Ie-23
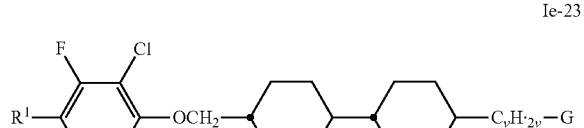
Ie-24
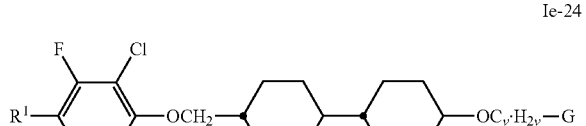
Ie-25
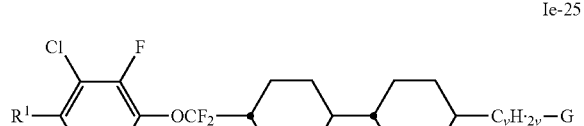
Ie-26
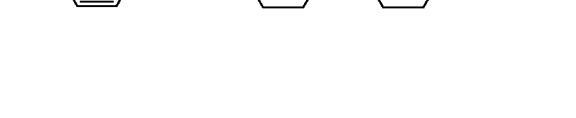
Ie-27
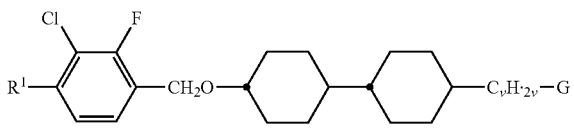
Ie-28
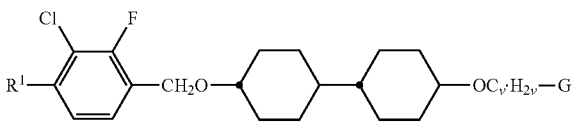
Ie-29
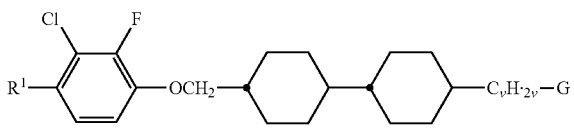
Ie-30
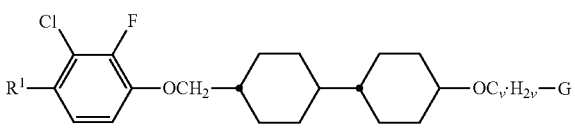
Ie-31
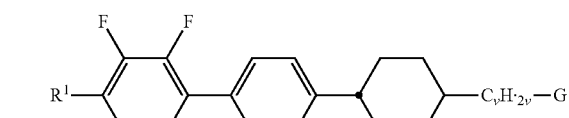
Ie-32
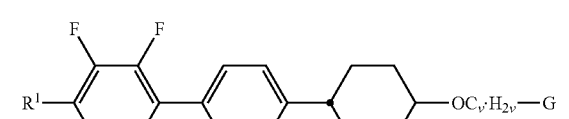
Ie-33
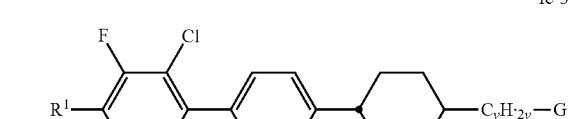
Ie-34
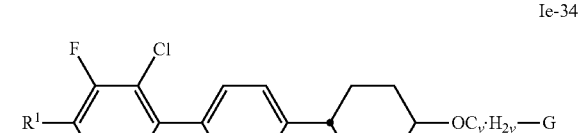
Ie-35
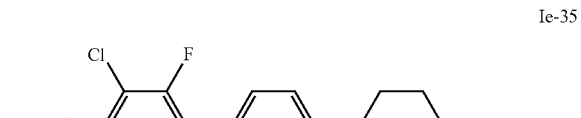
Ie-36
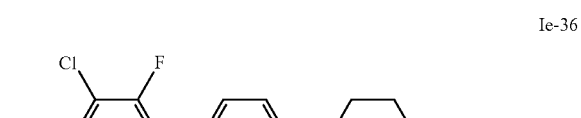
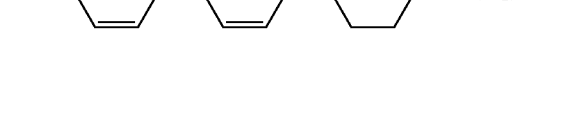

Ie-37
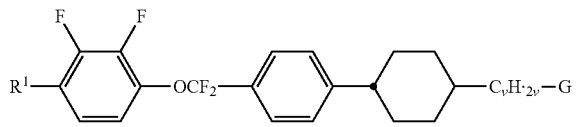
Ie-38
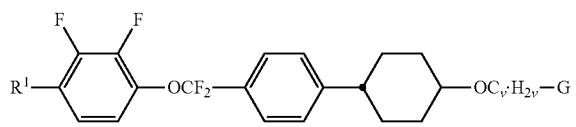
Ie-39
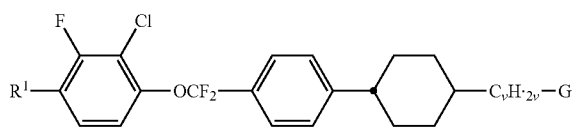
Ie-40
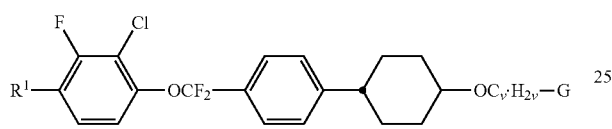
Ie-41
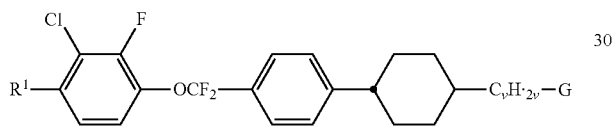
Ie-42
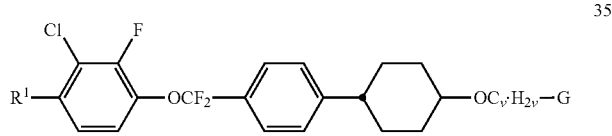
If-1
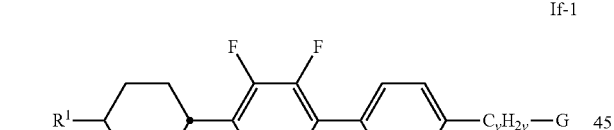
If-2
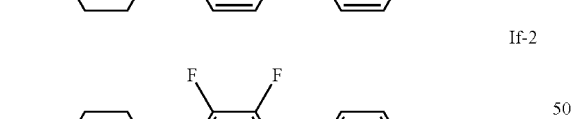
If-3
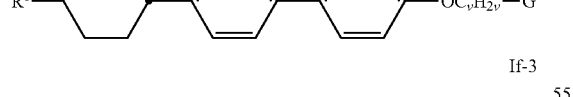
If-4
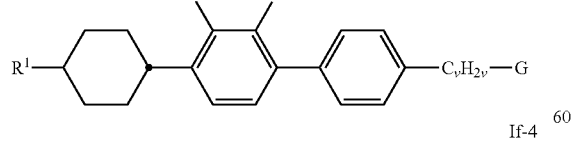
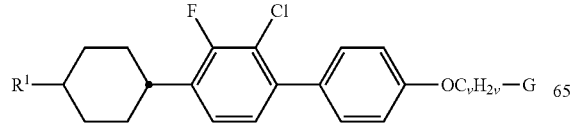
If-5
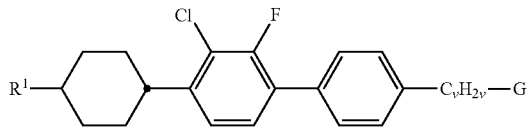
If-6
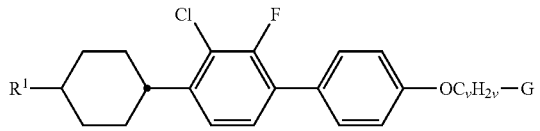
If-7
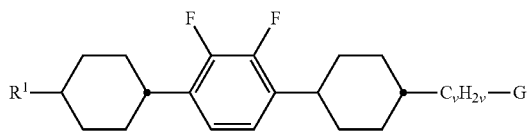
If-8
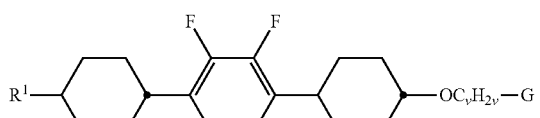
If-9
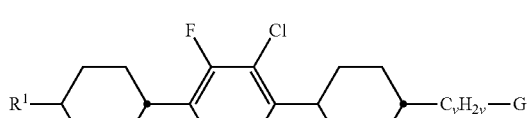
If-10
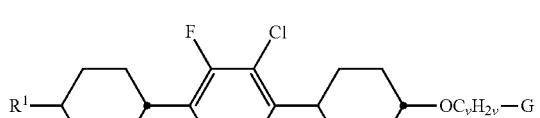
If-11
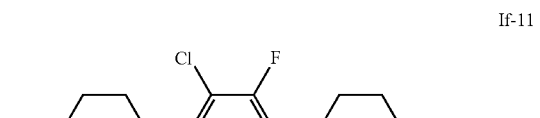
If-12
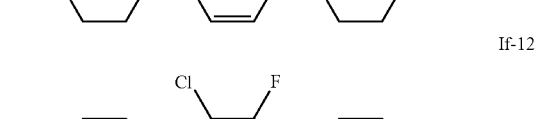
If-13
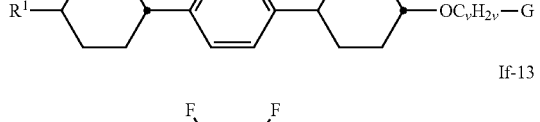
If-14
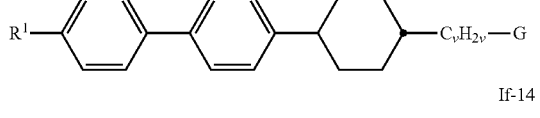

-continued

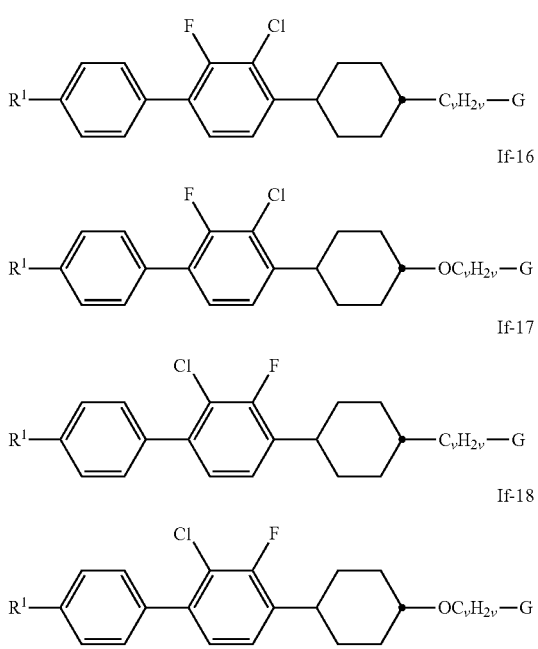

in which R¹ and G have the meanings given above and preferably
R¹ denotes alkyl having 1 to 7 C atoms and
G denotes —CH=CH₂, —P(O)(OH)₂ or —COH(P(O)(OH)₂)₂,
and
v denotes an integer from 1 to 12, preferably from 2 to 7.

Also covered by the description are compounds of the formula I in which the group —C$_v$H$_{2v}$— has been replaced by —C$_v$F$_{2v}$— in the sub-formulae Ia-1 to Ia-12, Ib-1 to Ib-32, Ic-1 to Ic-42, Id-1 to Id-34, Ie-1 to Ie-42 and If-1 to If-18.

Switching elements employed in accordance with the invention in the electronic component include a molecular layer comprising one or more compounds of the formula I.

The molecular layer of the present invention is a layer of electrically insulating, non-conducting and non-semiconducting organic compounds.

The molecular layer preferably comprises molecules of the formula I or, particularly preferably, consists of molecules of the formula I.

The thickness of the layer is preferably 10 nm or less, particularly preferably 5 nm or less, very particularly preferably 2 nm or less.

The molecular layer may consist of one, two, three or more molecule layers comprising compounds of the formula I.

The molecular layer employed in accordance with the invention is preferably a molecular monolayer.

In an embodiment, it is a self-assembled monolayer (SAM).

The production of self-assembled monolayers is known to the person skilled in the art; a review is given, for example, in A. Ulman, *Chem. Rev.* 1996, 96, 1533-1554.

In a further embodiment, the molecular layer is bonded to the substrate by chemisorption, in particular by an addition reaction or condensation reaction.

In a further embodiment, the molecular layer is bonded to the substrate by physisorption.

The degree of coverage of the substrate is preferably 90% or more to 100%, particularly preferably 95% or more to 100%, very particularly preferably 98% or more to 100%.

In a further embodiment, the molecular layer is covered with 1 to 10, preferably 1 to 5, particularly preferably 1 to 3, further layers of organic or inorganic adsorbates. Suitable layers comprise, for example, dielectrics, for example oxidic, fluoridic or nitridic materials, such as TiO₂, Al₂O₃, HfO₂, SiO₂, LiF and Si₃N₄, or metals, such as Pt, Pd, Pb, Au, Ag, Cu, Al and Mg, and eutectic compounds thereof, such as, for example, PdAu 20:80. Such layers can be built up in a thickness of a few nanometres by defined and high-precision deposition, for example by ALD (atomic layer deposition) processes.

The molecules of the molecular layer are preferably covalently bonded to the substrate. The bonding is carried out by known methods which are familiar to the person skilled in the art, for example by the addition reaction of a compound of the formula I or by esterification with hydroxyl groups located on the surface of the substrate.

For addition reactions, a suitable substrate, preferably a silicon surface—after corresponding pretreatment with aqueous NH₄F solution—can, for example, be treated in order to obtain a hydrogen-terminated surface. The surface treated in this way can then be treated at elevated temperature with exclusion of oxygen either directly with a suitable liquid compound of the formula I or a solution of the compound of the formula I in a suitable solvent.

For condensation reactions, a suitable substrate, preferably a silicon surface, can, for example, be treated with oxygen plasma in order to obtain a hydrophilic oxidic surface which is populated with hydroxyl groups. The surface treated in this way can then be prepared at elevated temperature either directly with a suitable, liquid compound of the formula I or a solution of the compound of the formula I in a suitable solvent. It is clear that an oxidic surface of this type merely serves for surface modification with the aim of possible derivatisation via condensation reactions and does not represent an insulator layer (14) in the true sense. Sufficiently large tunnel currents through this oxidic surface are possible owing to the low thickness in the order of 1 nm.

In the switching elements according to the invention, the molecules of the molecular layer are bonded to a substrate or an interlayer located between the molecular monolayer and the substrate. The substrate according to the invention can perform various functions, depending on the structure of the switching elements. For example, a conductive substrate can serve as first electrode. Likewise, the substrate can be a layer of a diode.

Suitable substrates are known to the person skilled in the art. Particularly suitable substrates are selected from:
  element semiconductors, such as Si, Ge, C (diamond, graphite, graphene, fullerene), α-Sn, B, Se and Te;
  compound semiconductors, preferably
    group III-V semiconductors, in particular GaAs, GaP, InP, InSb, InAs, GaSb, GaN, TaN, TiN, MoN, WN, AlN, InN, Al$_x$Ga$_{1-x}$As and In$_x$Ga$_{1-x}$Ni,
    group II-VI semiconductors, in particular ZnO, ZnS, ZnSe, ZnTe, CdS, CdSe, CdTe, Hg$_{(1-x)}$Cd$_{(x)}$Te, BeSe, BeTe$_x$ and HgS;
    group III-VI semiconductors, in particular GaS, GaSe, GaTe, InS, InSe$_x$ and InTe,
    group I-III-VI semiconductors, in particular CuInSe₂, CuInGaSe₂, CuInS₂ and CuInGaS₂,
    group IV-IV semiconductors, in particular SiC and SiGe,
    group IV-VI semiconductors, in particular SeTe;

organic semiconductors, in particular polythiophene, tetracene, pentacene, phthalocyanines, PTCDA, MePTCDI, quinacridone, acridone, indanthrone, flaranthrone, perinone, $AlO_3$, and mixed systems, in particular PEDOT:PSS and polyvinylcarbazole/TLNQ complexes;

metals, in particular Ta, Ti, Co, Mo, Pt, Ru, Au, Ag, Cu, Al, W and Mg;

conductive oxidic materials, in particular indium tin oxide (ITO), indium gallium oxide (IGO), InGa-α-ZnO (IGZO), aluminium-doped zinc oxide (AZO), tin-doped zinc oxide (TZO), fluorine-doped tin oxide (FTO) and antimony tin oxide.

The molecular layer may optionally also be bonded to a thin (preferably 0.5-5 nm thick) oxidic or fluoridic interlayer, for example $TiO_2$, $Al_2O_3$, $HfO_2$, $SiO_2$ or LiF, which is located on the substrate.

The counterelectrode or second electrode consists of a conducting or semiconducting material or a combination (layer stack) of a plurality of these materials. Examples are the materials mentioned as substrate material. Preference is given to Hg, In, Ga, InGa, Ag, Au, Cr, Pt, PdAu, Pb, Al, Mg, W, Yb, Zn, CNT (carbon nanotubes), graphene and conductive polymers (such as PEDOT:PSS).

In the following description of the illustrative embodiments of the invention, identical or similar components and elements are denoted by identical or similar reference numbers, where repeated description of these components or elements is avoided in individual cases. The figures only depict the subject-matter of the invention diagrammatically.

FIG. 1 shows a first embodiment of an electronic component in a sectional view from the side.

The electronic component (10) depicted in FIG. 1 is arranged on an outer substrate (12), which can be, for example, a wafer which has been provided with an insulator (14) on its side facing the other parts of the electronic component (10). The outer substrate (12) consists of the materials described above and is selected, for example, from an element semiconductor, such as silicon (Si), germanium (Ge), carbon in the form of diamond, graphite or graphene, from a compound semiconductor, in particular a II-VI compound semiconductor, such as cadmium selenide (CdSe), zinc sulfide (ZnS), from a metal, such as, for example, gold, silver, copper, aluminium, magnesium, or from a conductive oxidic material, such as indium tin oxide (ITO), indium gallium oxide (IGO), indium gallium zinc oxide (IGZO), aluminium-doped zinc oxide (AZO) or fluorine-doped tin oxide (FTO). Preference is given to the use of crystalline silicon as substrate, where silicon wafers having a (100) surface are particularly preferred. Silicon wafers whose surface is oriented at (100) are employed as conventional substrate in microelectronics and are available in high quality and with a low proportion of surface defects.

The insulator (14) can be, for example, an oxide, where this can be obtained, for example, on use of a silicon substrate by means of ion implantation of oxygen ions into the substrate. Second electrodes (20), which in the embodiment of FIG. 1 are implemented in the form of conductor tracks which run perpendicular to the drawing plane, are arranged on the insulator. In the embodiment depicted in FIG. 1, the first electrodes (20) are in the form of metallic electrodes. Diodes 22, which are, for example, in the form of Zener diodes and each comprise a highly p-doped layer 26 and a highly n-doped layer 24, are arranged on the first electrodes (20). A p-n junction of the diode 22 forms at the transition from the p-doped layer 26 to the n-doped layer 24.

The molecular layer (18) is arranged on the side of the diode (22), which forms the substrate according to the invention in this embodiment of the invention, facing away from the first electrodes (20). The molecular layer (18) is preferably in the form of a molecular monolayer and is thus precisely one layer of molecules thick.

A second electrode (16) (counterelectrode), which, like the first electrode (20), is in the form of a conductor track, is arranged on the side of the molecular layer 18 facing away from the diode (22). However, the second electrode (16) is rotated by 90° relative to the first electrode (20), so that a cross-shaped arrangement arises. This arrangement is also called a crossbar array, where the 90° angle is selected here as an example and arrangements in which second electrodes (16) and first electrodes (20) cross at an angle deviating from the right angle are also conceivable. A switching element (1), which is formed from a layer system having, in this sequence, a second electrode (16), a molecular layer (18) and a first electrode (20), is arranged at each crossing point between a second electrode (16) and a first electrode (20). In the embodiment depicted in FIG. 1, a diode (22) is also assigned to each switching element (1).

The crossbar array enables each switching element (1) to be addressed electrically by applying a voltage between the corresponding first electrode (20) and second electrode (16). Via the diodes (22), leakage currents are prevented from being able to flow over adjacent switching elements (1) here.

Owing to the bipolar switching characteristics of the switching elements (1), the diodes (22) must have non-linear characteristics for both polarities. To this end, the diodes (22) are, for example, in the form of Zener diodes, where for this purpose both the p-doped layer (26) and also the n-doped layer (24) are highly doped.

The structures of the electrodes (16, 20) can be produced by means of structuring methods known to the person skilled in the art from microelectronics. For example, a lithography method can be employed for the production of the first electrodes (20). In this, a metal layer is applied to the insulator (14) by means of vapour deposition. The metal layer is subsequently coated with a photoresist, which is exposed with the structures to be produced. After development and, where necessary, baking of the resist, the parts of the metal layer that are not required are removed, for example, by wet-chemical etching. The remaining resist is subsequently removed, for example using a solvent.

The structures of the second electrodes (16) can also be produced using a printing process, in which, in a similar manner to conventional printing, a conductive material is applied to the component (10) or to the molecular layer (18). Conductive polymers, such as poly(3,4-ethylenedioxythiophene)/polystyrene sulfonate (PEDEOT:PSS), for example, are suitable for this purpose.

A further possibility for the production of the electrodes (16, 20), in particular the second electrodes (16), is vapour deposition with the aid of a shadow mask. In this method, a mask whose openings correspond to the shape of the electrodes (16, 20) to be produced is placed on the component (10), and a metal is subsequently applied by vapour deposition. The metal vapour is only able to precipitate and form the electrode (16, 20) on the component (10) in the areas not covered by the mask.

Figure 2:
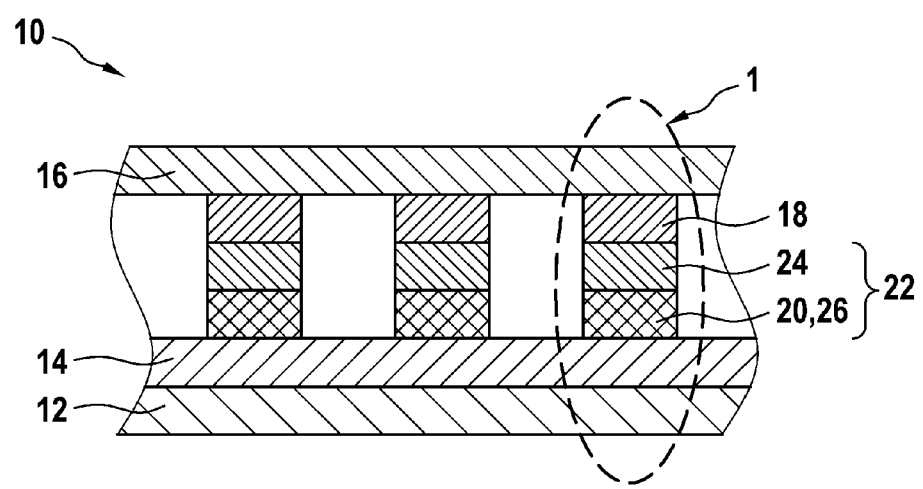
FIG. 2 shows a second embodiment of an electronic component.

FIG. 2 shows a further embodiment of the electronic component (10). In the embodiment of FIG. 2, the first electrodes (20) consist of a semiconductor material which is doped in order to function simultaneously as part of the diode (22). This embodiment is advantageous, in particular, in the case of the use of silicon-on-insulator wafers as outer substrate (12). A silicon-on-insulator wafer has a layer structure in which, in this sequence, layers of silicon, silicon dioxide and strongly doped silicon are arranged. A substrate of this type can be produced, for example, by firstly implanting with oxygen ions in the silicon substrate at a depth between 100 nm and 10 μm by means of ion implantation. Doping atoms are implanted close to the surface in order to establish p conduction or n conduction. After subsequent heat treatment, a layer of silicon dioxide then forms at a depth, since the implanted oxygen ions bond to the silicon. The silicon is used as substrate (12), while the silicon dioxide layer serves as insulator (14). The first electrodes (20) are produced from the doped silicon layer by means of conventional structuring methods known in principle from microelectronics. In continuation of this process, a p-n junction can also be produced directly at the surface of the silicon-on-insulator wafer. To this end, a plurality of ion implantation steps are carried out, where, in a first step, a p-doped layer, for example, is produced by volume implantation and an n-doped layer is subsequently produced by means of flat, surface implantation.

In the embodiment of FIG. 2, an n-doped layer (24) is arranged on the first electrodes (20), which also function as part of the diode (22). The first electrodes (20) are thus p-doped in order to form the diode (22) having a p-n junction together with the n-doped layer (24). In this embodiment, the n-doped layer (24) forms the substrate according to the invention.

The further layers are arranged as already described for FIG. 1, where in each case a switching element (1) is in turn formed at a crossing point of a first electrode (20) and a second electrode (16).

The compounds of the general formula I can be prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can be made here of variants known per se which are not mentioned here in greater detail.

If desired, the starting materials can also be formed in situ by not isolating them from the reaction mixture, but instead immediately converting them further into the compounds of the general formula I.

The syntheses of compounds of the general formula I according to the invention are described in illustrative terms in the examples. The starting substances can be obtained by generally accessible literature procedures or are commercially available.

Particularly suitable synthetic routes to the compounds according to the invention are illustrated below with reference to Schemes 1, 2 and 3 and are explained in greater detail with reference to the working examples.

The phosphonic acids according to the invention are preferably prepared by the Michaelis-Arbuzov reaction and subsequent acid-catalysed hydrolysis (Scheme 1).

Scheme 1

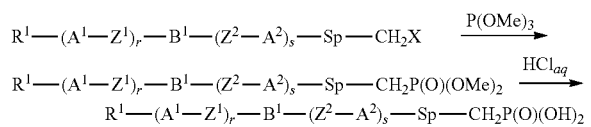

In Scheme 1, X denotes a leaving group, preferably Cl, Br, I, toluenesulfonyl or methanesulfonyl, particularly preferably Br.

Preferred synthetic methods for the preparation of the hydroxybisphosphonic acids according to the invention are described in M. Egorov, *Eur. J. Org. Chem.* 2011, 7148-7154; in a particularly preferred process, carboxylic acids are firstly derivatised using catecholborane and subsequently reacted with tris(trimethylsilyl) phosphite with decarboxylation followed by methanolysis give the hydroxybisphosphonates according to the invention (Scheme 2). Compounds containing perfluorinated spacer groups —Sp— are preferably prepared in accordance with A. Budinská, J. Václavík, V. Matoušek and P. Beier, *Org. Lett.* 2016, 18, 5844-5847, and as illustrated in Scheme 3. Chain lengths other than —CF$_2$CF$_2$— are accessible analogously.

Scheme 2

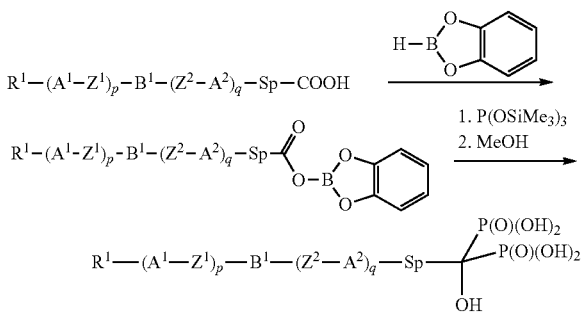

Scheme 3

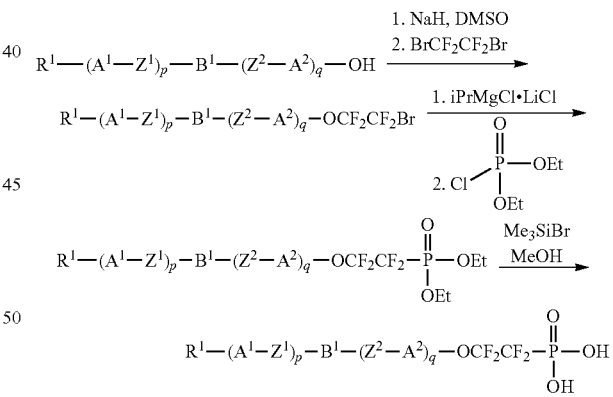

The invention is not restricted to the illustrative embodiments described here and the aspects emphasised therein. Instead, a multiplicity of modifications which are within the scope of action of the person skilled in the art are possible within the range indicated by the claims.

The invention is explained in greater detail by the examples, without restricting it thereby.

All physical properties are and have been determined in accordance with "Merck Liquid Crystals, Physical Properties of Liquid Crystals", Status November 1997, Merck KGaA, Darmstadt, Germany, and apply for a temperature of 20° C., and Δn is determined at 589 nm and Δε is determined at 1 kHz unless explicitly indicated otherwise in each case.

The liquid-crystalline properties of the individual compounds are, unless indicated otherwise, determined in the nematic host mixture ZLI-4792 (commercially available from Merck KGaA, Darmstadt) at a concentration of 10%.

EXAMPLES

1. Synthesis Examples

Substance Example 1: 1-But-3-enoxy-2,3-difluoro-4-[4-(4-methylcyclohexyl)cyclohexyl]benzene (CCY-5-O2V)

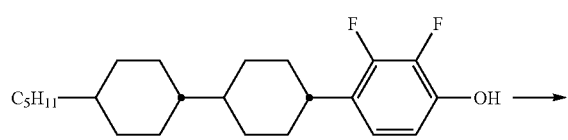

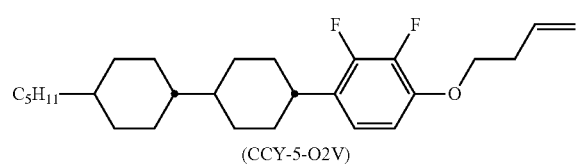

(CCY-5-O2V)

14.6 g (40 mmol) of 2,3-difluoro-4-[4-(4-pentylcyclohexyl)cyclohexyl]phenol are initially introduced in 100 ml methanol, firstly 8.9 ml of a 30 percent solution of sodium methoxide in methanol, 6.7 g (48 mmol) of 4-bromo-1-butene are subsequently added at 50° C., and the batch is left to stir under reflux for 6 h and then at room temperature overnight. The solvent is removed in vacuo, the residue is filtered through silica gel with toluene, and the crude product is recrystallised from ethanol, giving 1-but-3-enoxy-2,3-difluoro-4-[4-(4-methylcyclohexyl)cyclohexyl]benzene as a colourless solid.

Phase sequence: C 41 SmB 131 N 159 I.
Δε=−5.8

Substance Example 2: 1-But-3-enoxy-4-(4-butoxy-2,3-difluorophenyl)-2,3-difluorobenzene (YY-4O-O2V)

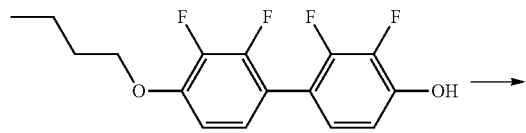

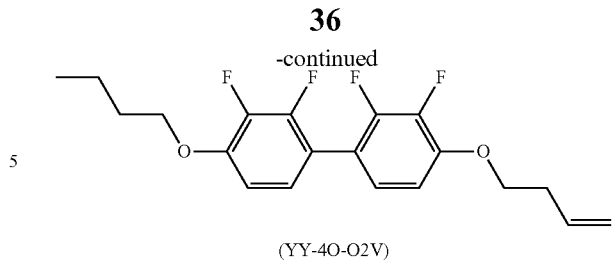

(YY-4O-O2V)

Analogously to the synthesis of Substance Example 1, 4-(4-butoxy-2,3-difluorophenyl)-2,3-difluorophenol gives 1-but-3-enoxy-4-(4-butoxy-2,3-difluorophenyl)-2,3-difluorobenzene as a colourless solid of m.p. 73° C. Δε=−11.9

Substance Examples 3 to 5 are prepared analogously to Substance Example 1.

Substance Example 3

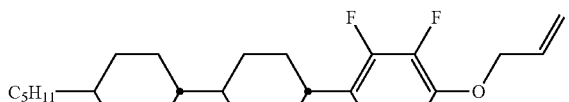

Phase sequence Tg −75 C 58 SmB 120 N 175 I
Δε=−5.7

Substance Example 4

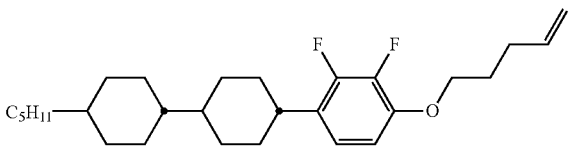

Phase sequence Tg −83 C 53 SmA1 127 SmA2 135 N 167 I

Substance Example 5

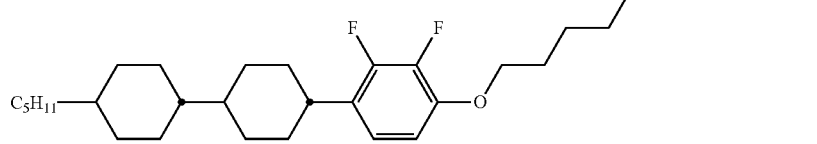

Phase sequence C 59 SmA 124 N 136 I

Substance Example 6: 3-[2,3-Difluoro-4-[4-(4-pentylcyclohexyl)cyclohexyl]phenoxy]propylphosphonic acid

Step 1: 1-(3-Bromopropoxy)-2,3-difluoro-4-[4-(4-pentylcyclohexyl)cyclohexyl]benzene (CCY-5-O3P)

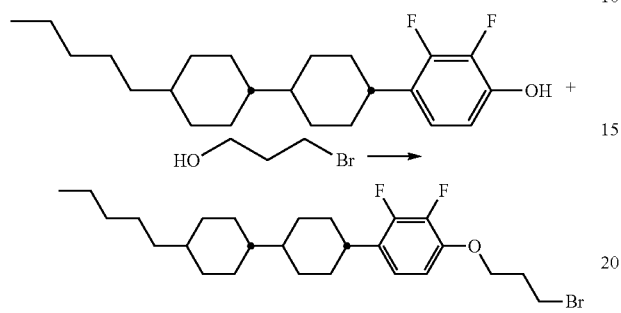

9.10 g (25.0 mmol) of 2,3-difluoro-4-[4-(4-pentylcyclohexyl)cyclohexyl]-phenol, 2.4 ml (27.6 mmol) of 3-bromo-1-propanol and 6.89 g (26 mmol) of triphenylphosphine are dissolved in 150 ml of THF, 5.50 ml (28 mmol) of diisopropyl azodicarboxylate are added dropwise with ice-cooling, and the mixture is left to stir at room temp. overnight. 200 ml of water and 100 ml of MTB ether are subsequently added to the batch, and the aqueous phase is separated off and extracted three times with MTB ether. The combined org. phases are washed with water and sat. sodium chloride soln. and dried over sodium sulfate. The solvent is removed in vacuo, and the residue is purified by chromatography on silica gel with n-heptane. Crystallisation from ethanol gives 1-(3-bromopropoxy)-2,3-difluoro-4-[4-(4-pentylcyclohexyl)cyclohexyl]benzene as colourless crystals.

Step 2: 1-(3-Diethoxyphosphorylpropoxy)-2,3-difluoro-4-[4-(4-pentylcyclohexyl)cyclohexyl]benzene

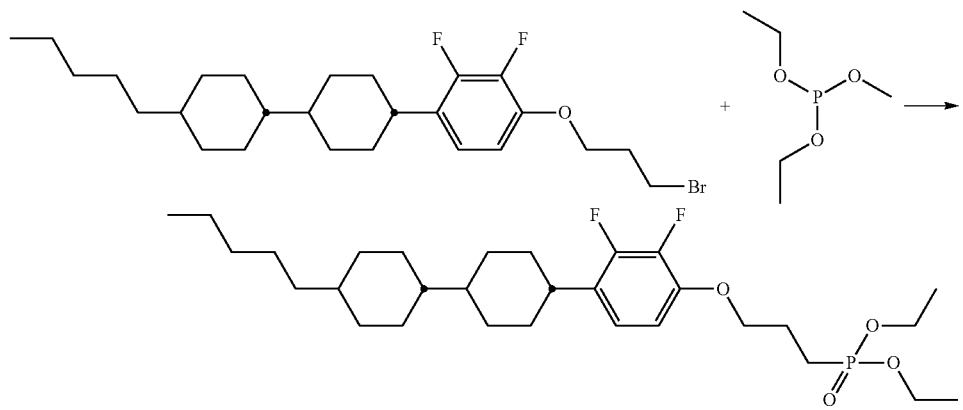

1.00 g (2.06 mmol) of 1-(3-bromopropoxy)-2,3-difluoro-4-[4-(4-pentylcyclohexyl)cyclohexyl]benzene and 1.1 ml (6.2 mmol) of triethyl phosphite are heated at 120° C. for 18 h and at 130° C. for 8 h. Excess triethyl phosphite is subsequently distilled off in a bulb tube, and the residue is chromatographed on silica gel with toluene/ethyl acetate (1:1) and subsequently ethyl acetate, giving 1-(3-diethoxyphosphorylpropoxy)-2,3-difluoro-4-[4-(4-pentylcyclohexyl)cyclohexyl]benzene as an amorphous colourless solid.

Step 3: 3-[2,3-Difluoro-4-[4-(4-pentylcyclohexyl)cyclohexyl]phenoxy]-propylphosphonic acid

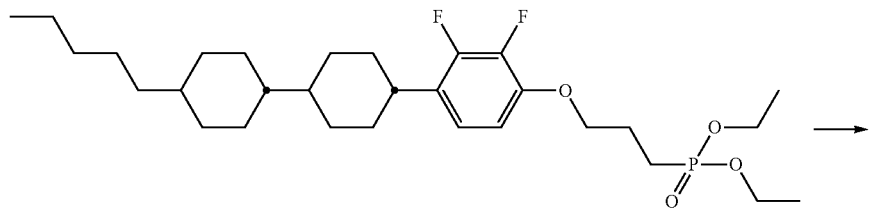

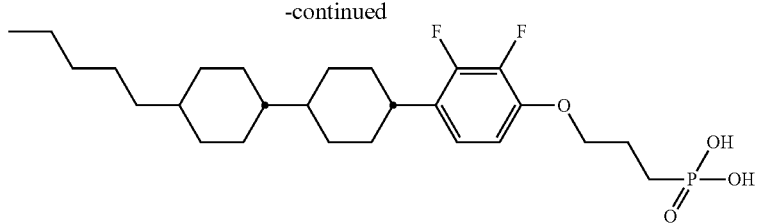

500 mg (0.921 mmol) of 1-(3-diethoxyphosphoryl-propoxy)-2,3-difluoro-4-[4-(4-pentylcyclohexyl)cyclohexyl]benzene is left to stir at 100° C. overnight in in 8 ml of conc. hydrochloric acid. The suspension is subsequently evaporated to dryness in vacuo, digested with cold water and acetone and dried in vacuo, giving 3-[2,3-difluoro-4-[4-(4-pentylcyclohexyl)cyclohexyl]-phenoxy]propylphosphonic acid as a colourless solid.

Phase sequence C 117 SmX 220 (decomp.)

Substance Examples 7 to 20 are prepared analogously to Example 6.

Substance Example 7

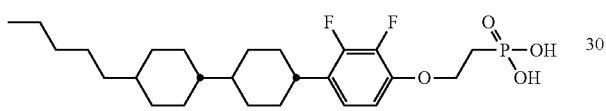

Phase sequence C 116 (decomp.)

Substance Example 8

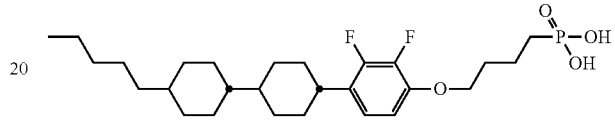

Phase sequence C 115 (decomp.)

Substance Example 9

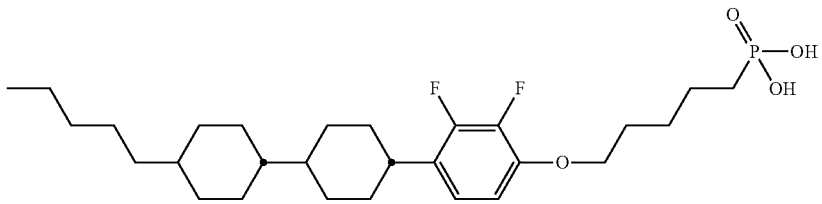

Phase sequence C 154 (decomp.)

Substance Example 10

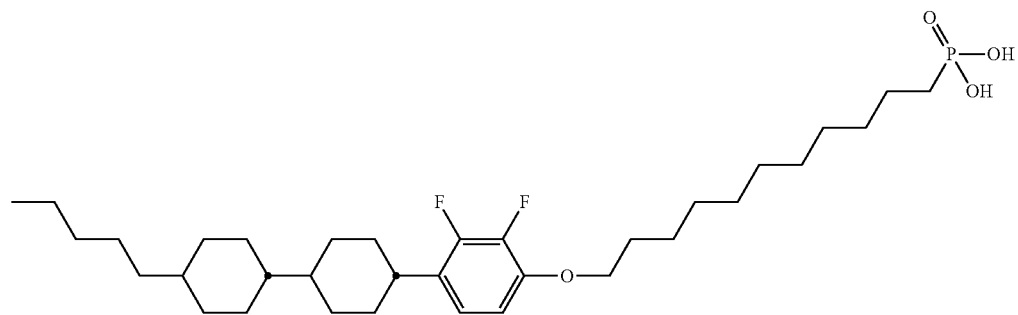

Phase sequence C 126 (decomp.)

Substance Example 11

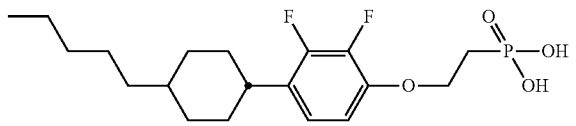

Phase sequence C 62 SmX (decomp.)

Substance Example 12

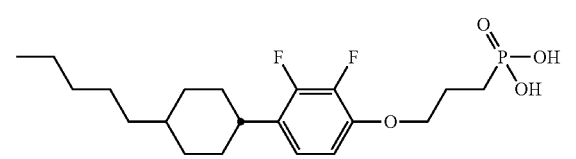

Phase sequence C 115 SmX (decomp.)

Substance Example 13

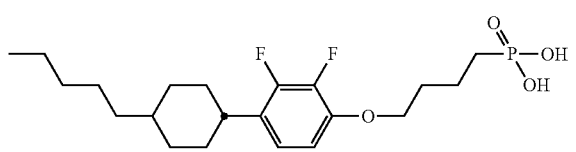

Phase sequence Tg −17 C 84 SmX (decomp.)

Substance Example 14

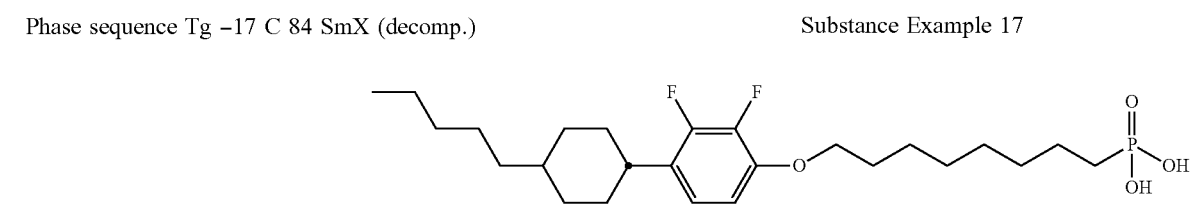

Phase sequence Tg −17 C 84 SmX (decomp.)

Substance Example 15

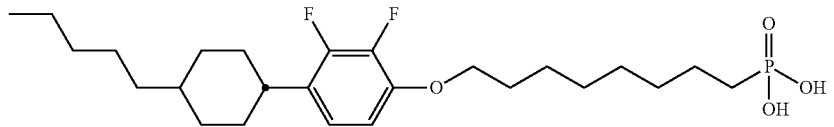

Phase sequence C 137 SmX 197 I (decomp.)

Substance Example 16

Phase sequence C 137 SmX 197 I (decomp.)

Substance Example 17

Phase sequence C 88 SmX 161 I

Substance Example 18

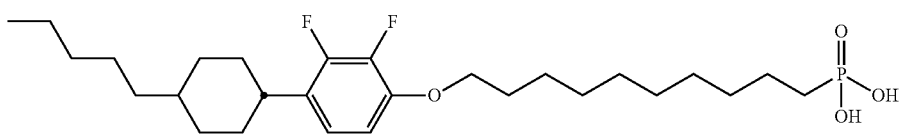

Phase sequence C 114 SmX 145 I

Substance Example 19

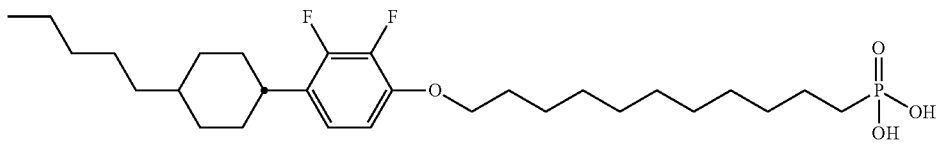

Phase sequence C 105 SmX (decomp.)

Substance Example 20

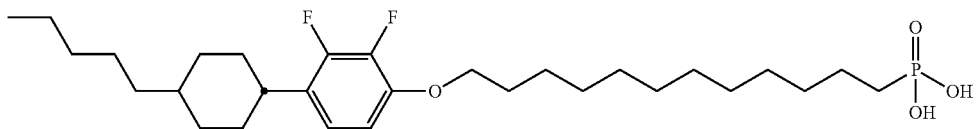

Phase sequence C 104 SmX 135 I

Substance Example 21: 5-[2,3-Difluoro-4-[4-(4-pentylcyclohexyl)cyclohexyl]phenoxy]butanoic acid Step 1: Ethyl 5-[2,3-difluoro-4-[4-(4-pentylcyclohexyl)cyclohexyl]phenoxy]-butanoate

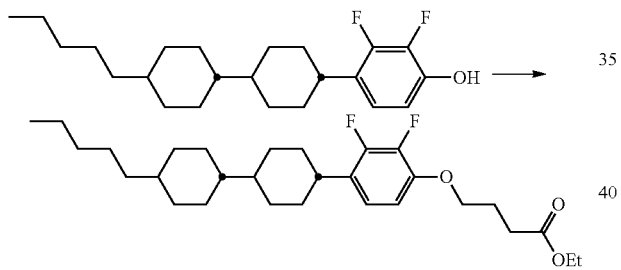

2,3-Difluoro-4-[4-(4-pentylcyclohexyl)cyclohexyl]phenol (6.0 g, 16.5 mmol) are initially introduced in acetone (60 ml) and, after addition of ethyl 4-bromobutyrate (6.4 g, 32.9 mmol) and K$_2$CO$_3$ (4.5 g, 32.9 mmol), heated under reflux for 16 h. The batch is subsequently filtered and evaporated, and the residue is filtered through silica gel with dichloromethane/heptane (1:1) and recrystallised from heptane, giving ethyl 5-[2,3-difluoro-4-[4-(4-pentylcyclohexyl)cyclohexyl]phenoxy]butanoate as colourless crystals.

Step 2: 5-[2,3-Difluoro-4-[4-(4-pentylcyclohexyl)cyclohexyl]phenoxy]-butanoic acid

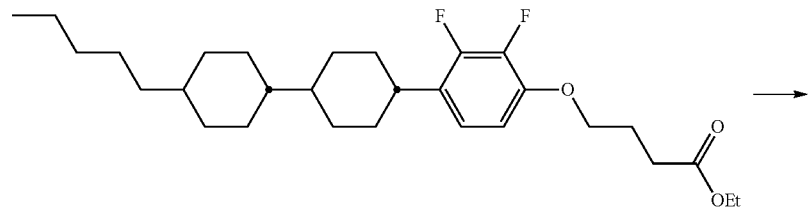

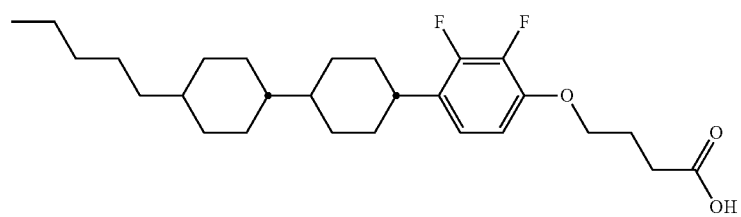

6.3 g (13.2 mmol) of ethyl 5-[2,3-difluoro-4-[4-(4-pentylcyclohexyl)cyclohexyl]phenoxy]butanoate are dissolved in THF (250 ml), 1 M LiOH (40 ml, 3 eqv.) Is added, and the batch is left to stir at 60° C. for 16 h. 250 ml of water are subsequently added, and the mixture is acidified using 3 equivalents of 2 N hydrochloric acid. The mixture is extracted with MTB ether, and the combined org. phases are washed with water and dried over magnesium sulfate. The solvent is removed in vacuo, and the residue is recrystallised from a mixture of 60 ml of dichloromethane and 100 ml of methanol, giving 5-[2,3-difluoro-4-[4-(4-pentylcyclohexyl)-cyclohexyl]-phenoxy]butanoic acid as colourless crystals.

Phase sequence: C 102 SmX 102 SmB 195 X 200 I (decomp.)

The following is obtained analogously to Substance Example 21:

Substance Example 22: 5-[2,3-Difluoro-4-[4-(4-pentylcyclohexyl)cyclohexyl]phenoxy]pentanoic acid

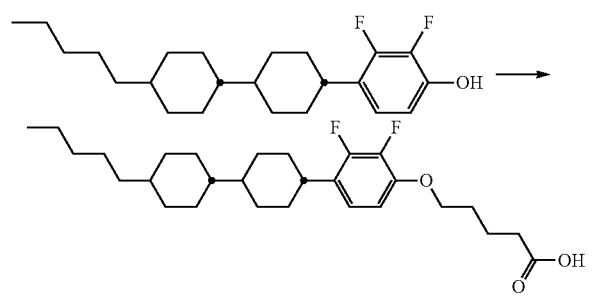

Phase sequence: C 151 SmX 202 N 221 I (decomp.)

Substance Example 23: [3-[2,3-Difluoro-4-[4-(4-pentylcyclohexyl)cyclohexyl]phenoxy]-1-hydroxy-1-phosphonopropyl]phosphonic acid

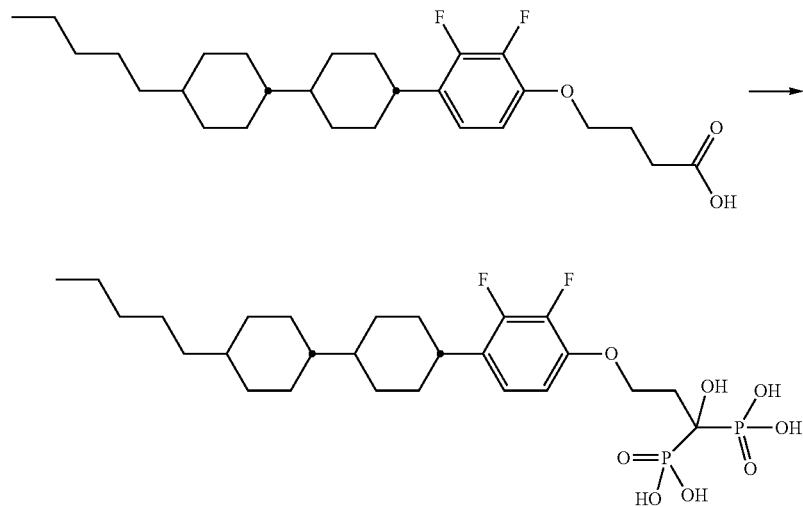

A 1 M solution of catecholborane in THF (1.35 ml, 1.35 mmol) is added at room temp. under argon to 546 mg (1.23 mmol) of 5-[2,3-difluoro-4-[4-(4-pentylcyclohexyl)cyclohexyl]phenoxy]butanoic acid. The batch is left to stir at room temp. for about 1 h until evolution of gas is no longer observed. 770 mg (2.58 mmol) of tristrimethylsilyl phosphite are subsequently added, and the batch is left to stir at room temp. overnight. After addition of 4 ml of methanol, the mixture is stirred for a further 1 h, and the solvent is removed in vacuo. The residue is covered with a layer of dichloromethane, and the solvent is decanted off. The oil which has deposited is taken up in a little methanol and diluted with ether, and the precipitated product is filtered off with suction, washed with ether and dried, giving [3-[2,3-difluoro-4-[4-(4-pentylcyclohexyl)cyclohexyl]phenoxy]-1-hydroxy-1-phosphonopropyl]phosphonic acid as colourless crystals.

Substance Example 24: (4-(2,3-Difluoro-4-(4'-pentyl-[1,1'-bi(cyclohexan)]-4-yl)phenoxy)-1-hydroxybutane-1,1-diyl)diphosphonic acid Step 1: 4-(2,3-Difluoro-4-(4'-pentyl-[1,1'-bi(cyclohexan)]-4-yl)phenoxy)butanoyl chloride

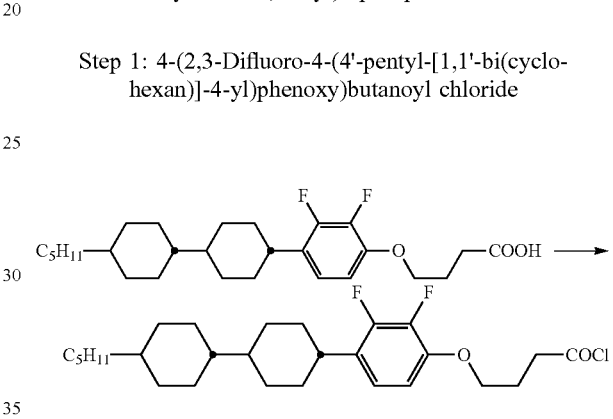

5.0 g (12 mmol) of 4-(2,3-difluoro-4-(4'-pentyl-[1,1'-bi(cyclohexan)]-4-yl)phenoxy)butanoic acid and 7.2 g of thionyl chloride (4.4 ml, 60 mmol) are heated under reflux in 20 ml of 1,2-dichloroethane (DCE) for 16 h. The batch is subsequently evaporated in vacuo, and the 4-(2,3-difluoro-4-(4'-pentyl-[1,1'-bi(cyclohexan)]-4-yl)phenoxy)butanoyl chloride is reacted further without further purification.

Step 2: (4-(2,3-Difluoro-4-(4'-pentyl-[1,1'-bi(cyclohexan)]-4-yl)phenoxy)-1-hydroxybutane-1,1-diyl)diphosphonic acid

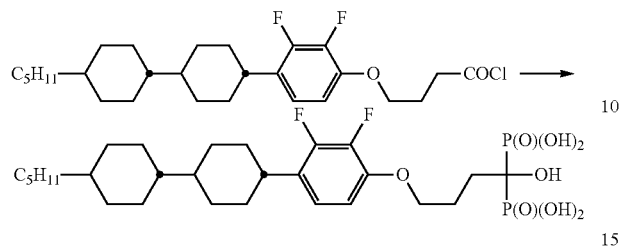

5.2 g (12 mmol) of 4-(2,3-difluoro-4-(4'-pentyl-[1,1'-bi(cyclohexan)]-4-yl)phenoxy)butanoyl chloride are initially introduced in 30 ml of tetrahydrofuran, and 7.9 g (26 mmol) of tris(trimethylsilyl) phosphite are added dropwise with ice-cooling. After 2 h, the cooling is removed, and the batch is stirred at room temp. for 8 h. The solution is evaporated in vacuo, and the residue is digested with methanol for 4 h. The precipitate obtained is filtered off, washed twice with methanol and dried in vacuo, giving (4-(2,3-difluoro-4-(4'-pentyl-[1,1'-bi(cyclohexan)]-4-yl)phenoxy)-1-hydroxybutane-1,1-diyl)diphosphonic acid as a colourless solid of m.p. 135° C.

The following are obtained analogously:

Substance Example 25

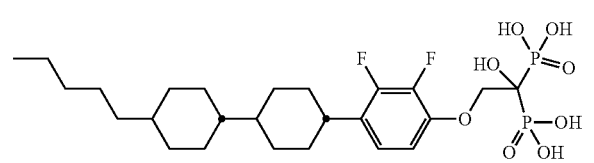

Phase sequence C 170 (decomp.)

Substance Example 26

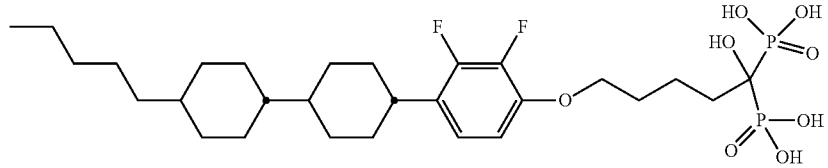

Substance Example 27

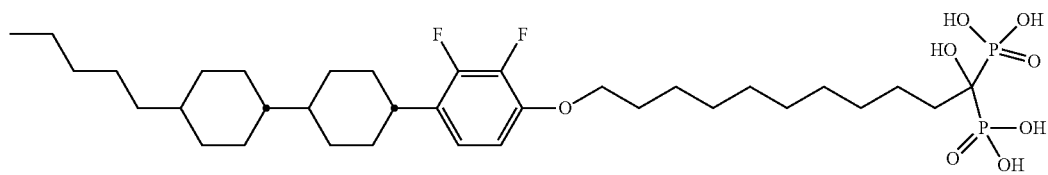

Phase sequence C 48 SmX 120 (decomp.)

Analogously to the syntheses described above, 2,3-difluorohydroquinone monoethyl ether gives the following compound:

Substance Example 28

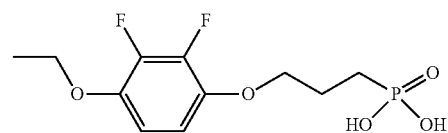 [SMILES: CCOc1ccc(OCCCP(=O)(O)O)c(F)c1F]

M.p. 93° C.

Substance Example 29: [2-[2,3-Difluoro-4-(4-pentylcyclohexyl)phenoxy]-1,1,2,2-tetrafluoroethyl]phosphonic acid Step 1: 1-(2-Bromo-1,1,2,2-tetrafluoroethoxy)-2,3-difluoro-4-(4-pentylcyclohexyl)benzene

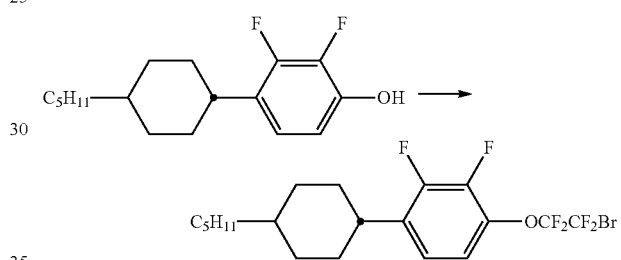

6.0 g (21 mmol) of 2,3-difluoro-4-(4-pentylcyclohexyl)phenol are initially introduced in 40 ml of dimethyl sulfoxide under argon, and sodium hydride (1.0 g, 25 mmol, 60% dispersion in mineral oil) is added in portions at room temp. When the addition is complete, the batch is left to stir for 30 min., 1,2-dibromotetrafluoroethane (10.9 g) is added slowly, and the mixture is subsequently warmed at 60° C. for 6 h. After cooling, the batch is diluted with 120 ml of water and extracted three times with 50 ml of petroleum ether. The combined org. phases are evaporated in vacuo, and the crude product is chromatographed on silica gel with petroleum ether, giving 1-(2-bromo-1,1,2,2-tetrafluoroethoxy)-2,3-difluoro-4-(4-pentylcyclohexyl)benzene as a colourless solid.

Step 2: 1-(2-Diethoxyphosphoryl-1,1,2,2-tetrafluoroethoxy)-2,3-difluoro-4-(4-pentylcyclohexyl)benzene

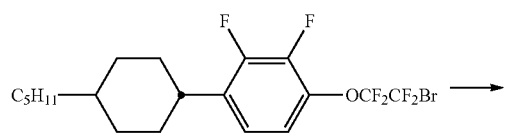

-continued

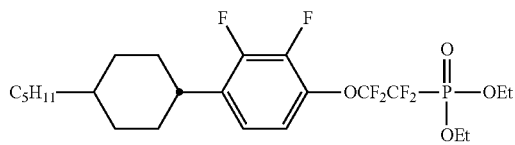

2.0 g (4.3 mmol) of 1-(2-bromo-1,1,2,2-tetrafluoroethoxy)-2,3-difluoro-4-(4-pentylcyclohexyl)benzene is initially introduced in 20 ml of tetrahydrofuran (THF) at −78° C., and a 1.3 M solution of i-PrMgCl.LiCl in THF is added. After 3 min, 1.1 equivalents of diethyl chlorophosphonate in THF are added, the cooling is removed, and the batch is left to stir at room temp. for 1 h. After aqueous work-up, the crude product is chromatographed with petroleum ether/ethyl acetate (3:1) and silica gel, giving 1-(2-diethoxyphosphoryl-1,1,2,2-tetrafluoroethoxy)-2,3-difluoro-4-(4-pentylcyclohexyl)benzene as a yellow oil.

Step 3: [2-[2,3-Difluoro-4-(4-pentylcyclohexyl)phenoxy]-1,1,2,2-tetrafluoroethyl]phosphonic acid

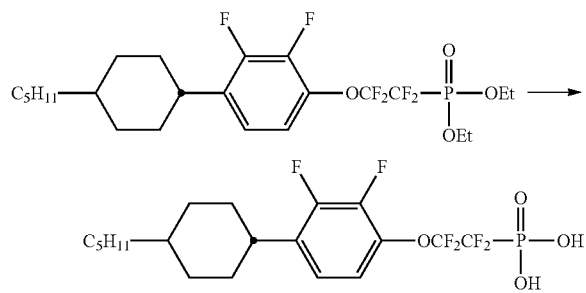

Bromotrimethylsilane (5.20 g, 34 mmol) is added dropwise under argon to 1-(2-diethoxyphosphoryl-1,1,2,2-tetrafluoroethoxy)-2,3-difluoro-4-(4-pentylcyclohexyl)benzene (1.63 g, 3.4 mmol), and the mixture is heated under reflux for 12 h. The volatile constituents are subsequently removed in a fine vacuum, and the crude product is digested with methanol at room temp. for 8 h. The solvent is subsequently removed in vacuo, giving [2-[2,3-difluoro-4-(4-pentylcyclohexyl)phenoxy]-1,1,2,2-tetrafluoroethyl] phosphonic acid as a colourless solid.

Phase sequence C 65 SmX 112 N 140 I

A reference compound of the formula

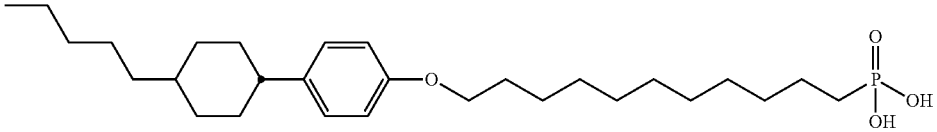

(CP-5-O11P)

is prepared like Substance Example 19.

2. Use Examples

Derivatisation of Silicon Surfaces by Si—C Linking

In principle, the derivatisation of silicon surfaces here is carried out analogously to O. Seitz et al., Langmuir 22 (2006), 6915-6922. Firstly, organic impurities are removed from the silicon substrate using acetone in an ultrasound bath, and the substrate is then treated with piranha (conc. $H_2SO_4$/30% $H_2O_2$ 70:30). After rinsing with water, the substrate is treated with aqueous $NH_4F$ solution with exclusion of oxygen and subsequently washed with oxygen-free water. The substrate, which is now hydrogen-terminated, is treated with a 10% solution of the derivatisation reagent in 1,2-dichlorobenzene at 120° C. for 12 h with strict exclusion of oxygen. Liquid derivatisation reagents can also be used without solvents. The derivatised substrate is subsequently washed with acetone in an ultrasound bath, rinsed with isopropanol and dried using a jet of nitrogen in a dust-free environment.

Procedure

A freshly produced, hydrogen-terminated chip (8 mm×8 mm×575±25 μm, 100 orientation, doped with boron to a high degree) is heated with degassed derivatisation reagent (for example a 10 percent (w/w) solution of 1-but-3-enoxy-2,3-difluoro-4-[4-(4-methylcyclohexyl)cyclohexyl]benzene from Substance Example 1 in 1,2-dichlorobenzene) in an argon-flushed Schlenk vessel at 110° C. for 18 h. The chip, which was now organo-modified, was removed from the reaction vessel, rinsed with acetone in an ultrasound bath for 5 min, rinsed with acetone and isopropanol, and dried in a stream of nitrogen. The derivatised chip is stored in an Eppendorf vessel.

Derivatisation of Silicon Surfaces by Si—O Linking

The derivatisation of silicon surfaces by formation of an Si—O link is preferably carried out by hydrophilisation using oxygen plasma in order to generate a hydroxyl-containing silicon oxide surface and subsequent esterification using suitable derivatisation reagents, such as phosphonic acids, phosphoric acids, carboxylic acid, alcohols, trialkoysilanes, trichlorosilanes, etc. Treatment of this type is explained in greater detail below for the example of the reaction with phosphonic acids.

Derivatisation of Silicon Surfaces by Means of an Aluminium Oxide Interlayer

Here, a silicon wafer is coated by an ALD (atomic layer deposition) process with an $Al_2O_3$ layer having a thickness of, for example, 2 nm, which can be derivatised in a second step using suitable derivatisation reagents which have already been described for silicon dioxide surfaces. In a preferred process, $Al_2O_3$ is deposited on the wafer surface by a wet-chemical method with the aid of the precursor substances trimethylaluminium and water. Treatment of this type is explained in greater detail below for the example of the reaction with phosphonic acids.

Topographic and Electrical Characterisation

A memristive switching behaviour was measured for a number of dipolar monolayer systems so that they could be verified as illustrative embodiments according to the invention. All layers were prepared on p+ Si (100) substrates. The organic groups indicated in the third column of the following table were achieved as monolayers, with the precursors indicated in the second column being employed for this purpose.

| Example | Precursor | Monolayer |
| --- | --- | --- |
| 1 | Substance Example 1 (CCY-5-O2V) | 2,3-Difluoro-4-[4-(4-pentylcyclohexyl)cyclohexyl]-1-phenoxybutyl (CCY-5-O4) |
| 2 | Substance Example 2 (YY-4O-O2V) | 1-But-3-enoxy-4-(4-butoxy-2,3-difluorophenyl)-2,3-difluoro-benzene (YY-4O-O4) |
| 3 | Substance Example 6 (CCY-5-O3P) | 2,3-Difluoro-4-[4-(4-pentylcyclohexyl)cyclohexyl]-1-phenoxypropylphosphonate (CCY-5-O3P) |
| 4 | Substance Example 19 (CY-5-O11P) | 11-[2,3-Difluoro-4-(4-pentylcyclohexyl)phenoxy]undecylphosphonic acid (CY-5-O11P) |

The electrical measurements on various samples are described below with reference to FIGS. 3 to 16.

Figure 3:
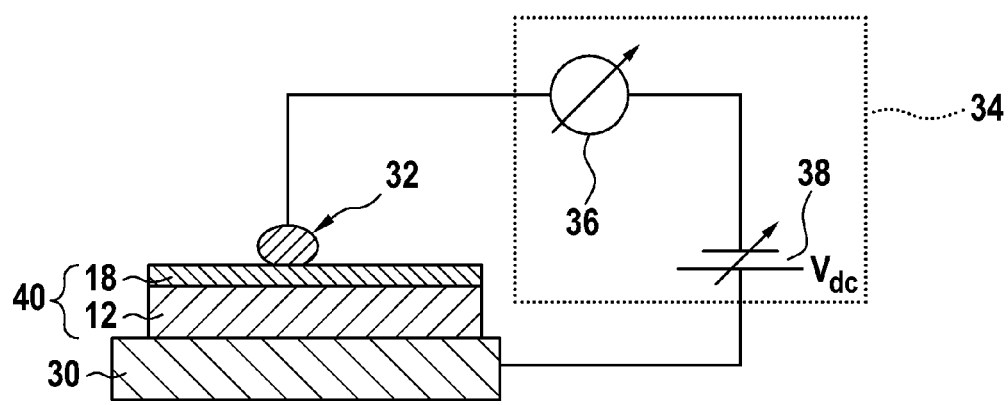
FIG. 3 shows a diagrammatic representation of an experimental set-up for electrical characterisation.

FIG. 3 shows an experimental set-up for characterisation of the electrical properties of a molecular layer on a substrate.

FIG. 3 shows diagrammatically how the electrical properties of a sample (40) are determined. The sample (40) comprises the substrate (10), to which a molecular layer (18) has been applied. The substrate (10) is electrically conductive and serves here as an electrode in order to provide electrical contact for the molecular layer (18). The electrical connection to a measuring instrument (34) is established here via a movable copper plate (30). To this end, the sample (40) is placed on the copper plate (30) and can be moved relative to a further electrode by moving the copper plate (30). The further electrode used for electrical contacting of the top side of the molecular layer (18) is a suspended mercury drop (32), which is likewise connected to the measuring instrument (34) via its suspension. The diameter of the mercury drop (32) is typically about 150 µm.

After the sample (40) has been placed on the copper plate (30), the latter is moved in relation to the mercury drop (32) in such a way that the mercury drop (32) touches the surface of the molecular layer (18). This enables non-destructive and interaction-free testing of the electrical conductivity properties of the sample (40).

For the electrical measurements, the measuring instrument (34) is preferably designed as a source measure unit, i.e. the measuring instrument (34) provides an output voltage via a voltage source (38) and simultaneously measures the resultant electric current via a current measuring unit (36).

Figure 4:
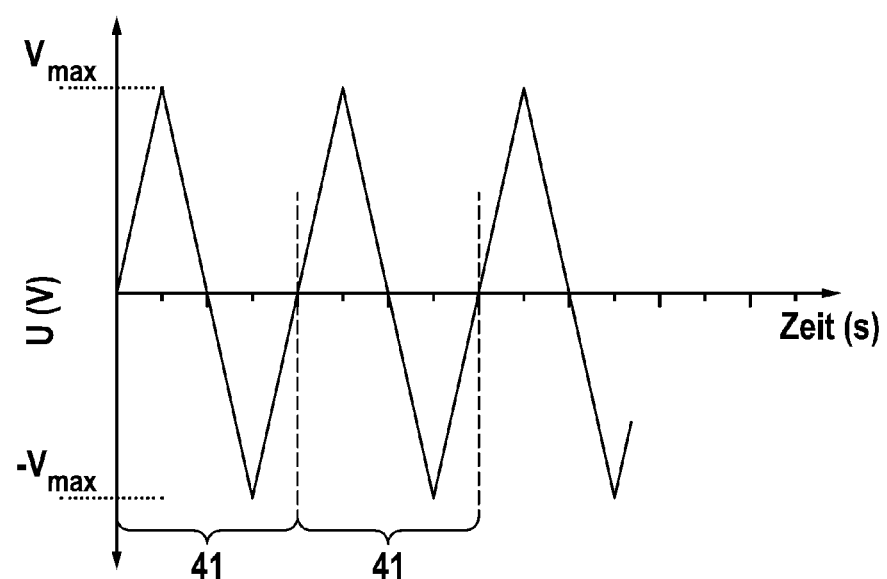
FIG. 4 shows a diagram which represents a cyclically varied voltage.

For the measurements, an electrical voltage is applied between the copper plate (30) and the mercury drop (32) and varied, at the same time the electric current through the sample (40) is measured. The voltage varies cyclically between a pre-specified maximum value $V_{max}$ and a pre-specified minimum value $V_{min}$, as shown in FIG. 4. The experiments were carried out using a source measure unit of the Keithley 2635 type.

FIG. 4 shows by way of example a number of cycles (41) in which the applied voltage is varied cyclically between $V_{max}$ and $V_{min}$, with a sawtooth-shaped voltage curve forming.

A direct voltage is applied to the two electrodes (the substrate (12) and the mercury drop (32), see FIG. 3) via the measuring instrument (34) and varied over time in a cyclic sequence at constant rate, for example 5 mV/s, between a maximum negative and maximum positive voltage value. Three such cycles (41) are shown in FIG. 4. The resultant current through the sample (10) to be characterised is measured and recorded.

The recorded currents for various samples are shown in the following figures and explained in greater detail in the associated description.

Figure 5:
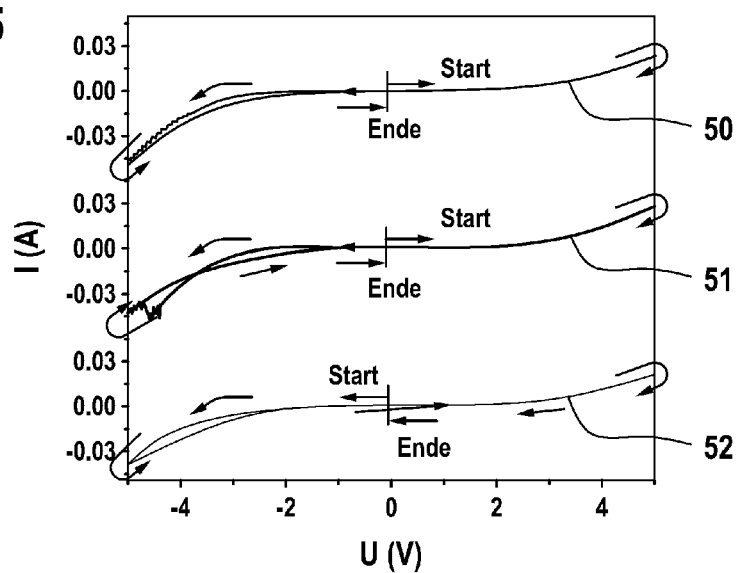
FIG. 5 shows the recorded current through three samples each having a monolayer system produced from compound CCY5-O2V.

FIG. 5 shows the recorded current as a function of the applied voltage through three different samples having the monolayer system CCY-5-O4. A characteristic, weak hysteretic behaviour in the region of negative pre-voltages of the substrate is evident.

The low currents measured here can be particularly advantageously for memory applications. ON currents typically measured in the case of memristors on the basis of the formation of metal filaments are very high (100 mA region) and represent a particular problem in electronic circuits (for example power consumption, evolution of heat). The $R_{HRS}$:$R_{LRS}$ ratio of the CCY-5-O4 system, measured by means of an Hg electrode, is about 1.4 (reading voltage −4 V).

Electrical Measurements with Permanent Second Electrode

Instead of the Hg electrode (cf. FIG. 3), permanent, thin metal films comprising Pb (200 nm) followed by Ag (150 nm) were applied to a YY-4O-O4 sample by the shadow vapour deposition technique. The upper electrodes (80 µm×80 µm) prepared in this way are provided with a measurement needle contact. Otherwise, the electrical measurements are carried out analogously to the arrangement or procedure described above.

Figure 6:
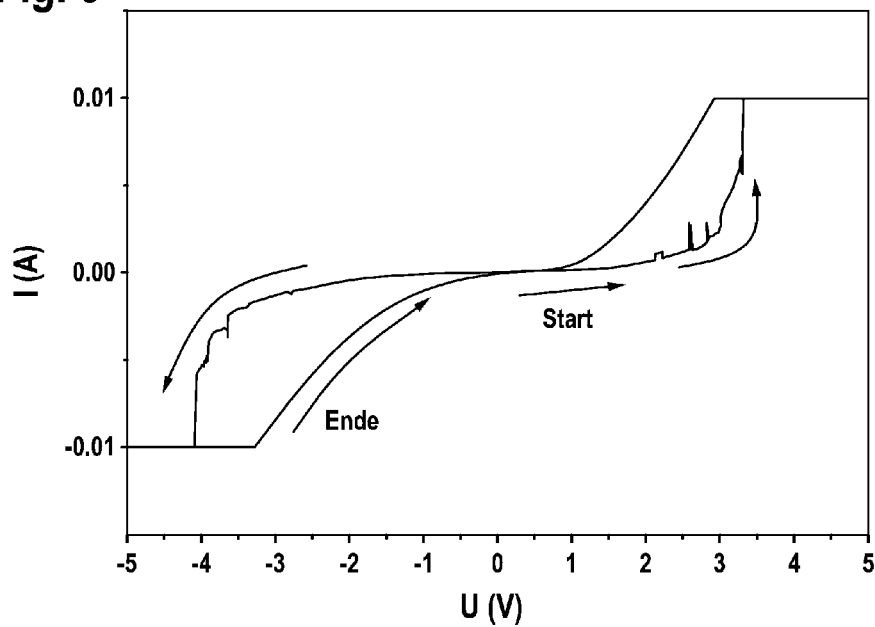
FIG. 6 shows the recorded current through a sample having a monolayer system produced from compound YY-4O-O2V with a permanent second electrode comprising Pb/Ag.
Figure 7:
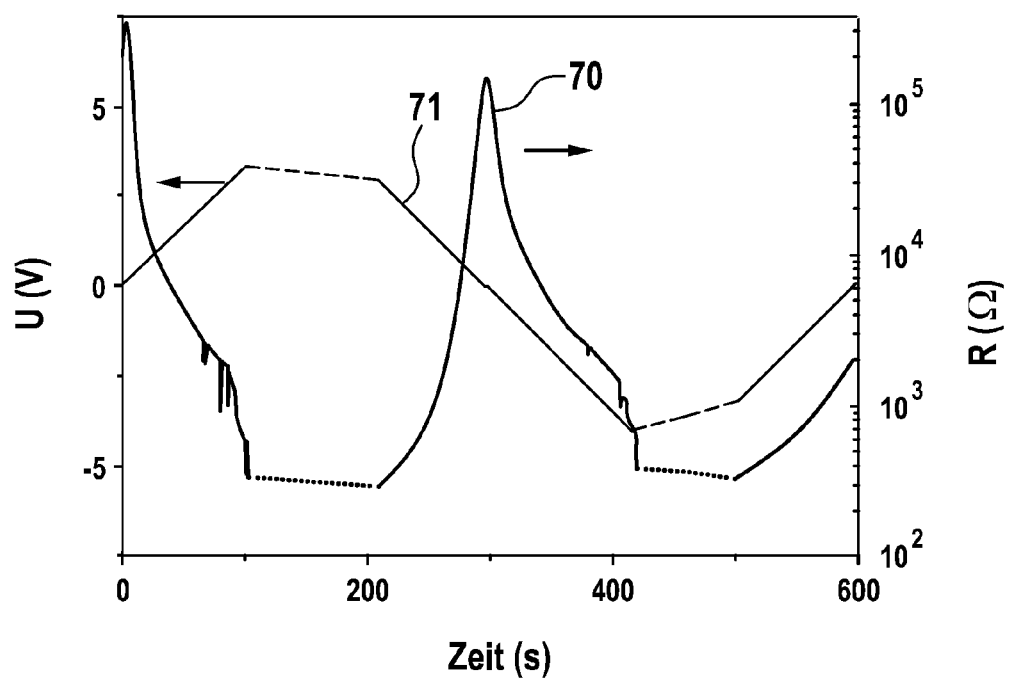
FIG. 7 shows the applied voltage and the measured resistance as a function of time for a sample having a monolayer system produced from compound YY-4O-O2V (one measurement cycle)

FIG. 6 shows the characteristic switching behaviour with pronounced hysteresis for this system, which can be reproduced on the basis of at least 4 test cycles following from one another, without significant degradation of the effect or sample occurring. In order to protect the memristive structure against possible degradation or destruction by excessively high currents, the maximum current is limited to +/−10 mA ("current compliance"). The OFF/ON ratio of the two resistance values der $R_{HRS}$:$R_{LRS}$ is about ~2 (at a reading voltage of +0.05 V) or ~70 (at −0.05 V). FIG. 7 shows the characteristic variation of the resistance (70) as a function of time over a voltage cycle (71).

Production and Characterisation of a Crossbar Array Using Phosphonic Acids

Component Production

The production of the components comprises at least the following steps:
i. wafer treatment for the production of the first electrodes (20)
ii. deposition of the phosphonic acid monolayer (18)
iii. application of a second electrode (16)

The process steps are described in detail below:

i. Wafer Treatment for the Production of the First Electrodes (20)

The starting material is a silicon-on-insulator wafer ("SOI wafer") with a diameter of 6 inches, having a silicon layer with a thickness of 110 nm with [100] orientation on a silicon oxide layer with a thickness of 200 nm on a slightly boron-doped silicon wafer with a thickness of 525 µm with [100] orientation and a resistivity of about 20 Ωcm.

The upper silicon layer has been highly boron-doped by ion implantation (doping concentration $c\sim5\times10^{19}$ $cm^{-3}$, resistivity $\rho\sim1.4$ mΩ·cm). After doping, the wafer is divided into square parts ("chips") measuring 8 mm×8 mm. The chips are cleaned firstly in acetone and subsequently in isopropanol in an ultrasound bath for 10 min in each case.

The structuring for the production of the silicon conductor tracks the first electrodes (20) is carried out by photolithography and subsequent selective dry etching by means of reactive ions. Eight silicon conductor tracks are produced in the present example For contacting of the silicon conductor tracks, square contact areas 200 consisting of a layer of chromium (10 nm) followed by gold (130 nm) are applied alternately to the ends of conductor tracks in a second analogous photolithography step by electron beam evaporation, and the photoresist is removed. Various chips having a width of the silicon conductor tracks of in each case 25 µm, 35 µm and 50 µm are produced.

ii. Deposition of the Phosphonic Acid Monolayer (18)

The chips freshly produced as described above are cleaned again in acetone and isopropanol in an ultrasound bath for 5 min in each case and subsequently treated with piranha solution at 70° C. After rinsing with deionised water, the chips are treated with oxygen plasma (200 W, 7 min), producing a hydroxyl-populated silicon dioxide layer on the silicon conductor tracks, which hydrophilises the surface and makes it reactive to, for example, phosphonic acids.

For the deposition of the phosphonic acid monolayer (18) on the silicon conductor tracks (20), the chips are subsequently dip-coated with a 250 µM solution of CCY-5-O3P (Substance Example 6) in tetrahydrofuran, then heated at 120° C. in an oven overnight and then washed with ethanol. This process essentially corresponds to the "TBAG" method known from the literature and gives a self-arranged monolayer (SAM) (18) of, in the present example, CCY-5-O3P.

iii. Application of a Second Electrode

Second electrodes (16) of lead having a thickness of 200 nm are vapour-deposited on the monolayer (18) produced as described under steps i. and ii. on the first electrode (20) through a shadow mask at a deposition rate of 5 Å/s. The shadow mask is available in various embodiments and has parallel slots having a width of either 25 µm, 35 µm or 50 µm, corresponding to the width of the silicon strips of the first electrodes (20), which have larger square cut-outs at the ends, resulting in square contact areas (160), likewise of lead, being produced in the same process step for later contacting of the ends of the conductor tracks. In the present example, eight lead conductor tracks are vapour-deposited perpendicular to the eight silicon conductor tracks, giving rise to 64 switching elements (1) according to the invention at the respective crossing points.

Figure 8A:
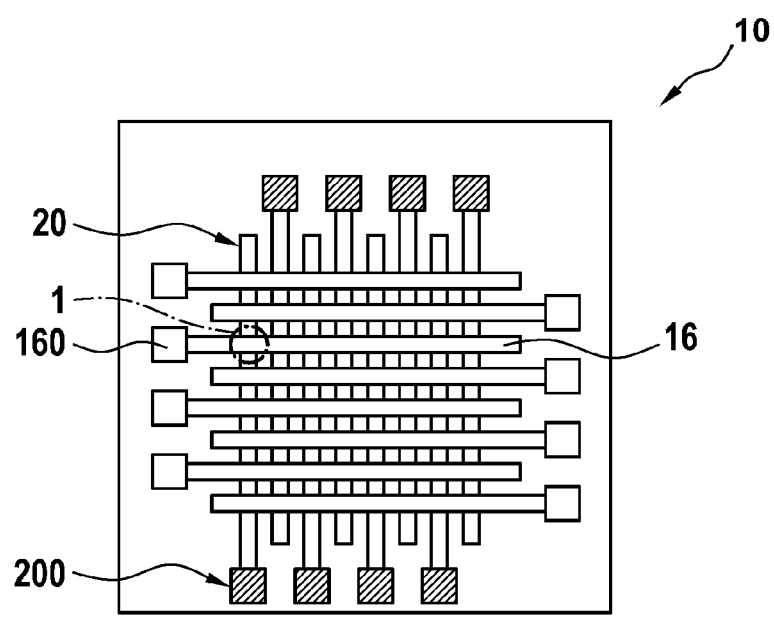
FIG. 8a shows a plan view of a crossbar array according to the invention.
Figure 8B:
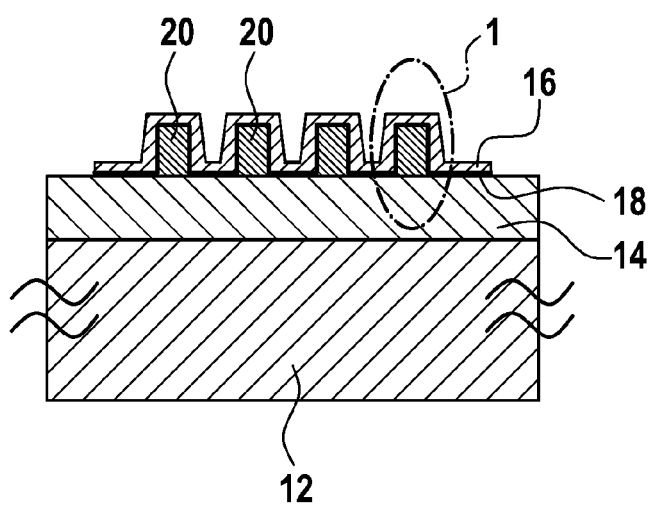
FIG. 8b shows a side view of a longitudinal section of a crossbar array according to the invention along a second electrode.
Figure 9:
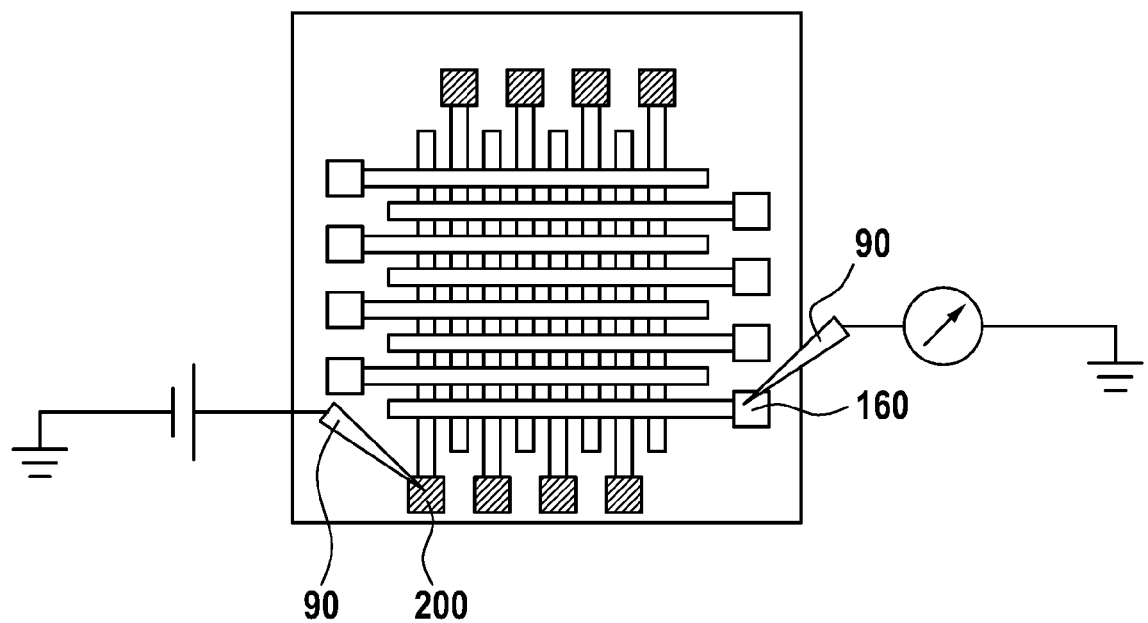
FIG. 9 shows a diagrammatic representation of the contacting of a switching element according to the invention.

FIG. 8a shows a plan view of a diagrammatic representation of the crossbar array produced in the manner described above, where, for reasons of clarity, the depiction of the molecular layer (18) has been omitted. FIG. 8b shows a side view of the same crossbar array in longitudinal section along a second electrode (16).

Electrical Measurements and Characterisation

For contacting of the crossbar array according to the invention, a measurement device is fitted with berylium/copper contact needles (90) having a tip diameter of 25 µm. By contacting of in each case a first electrode (20) (in the present case comprising silicon) on the corresponding contact area (200) with a first contact needle (90) and a second electrode (16) (in the present case comprising lead) on the corresponding contact area (160) with a second contact needle (90), all 64 switching elements (1) can be measured successively. A measurement arrangement of this type is depicted by example in FIG. 9. For electrical characterisation of the crossbar array according to the invention, cyclic current/voltage curves are recorded in vacuo ($\sim3\cdot10^{-6}$ mbar, 20° C.) using a Keithley 2635 SMU. The respective second electrode (16) was earthed and the pre-voltage was applied to the respective first electrode (20).

Measurement Results

Figure 10A:
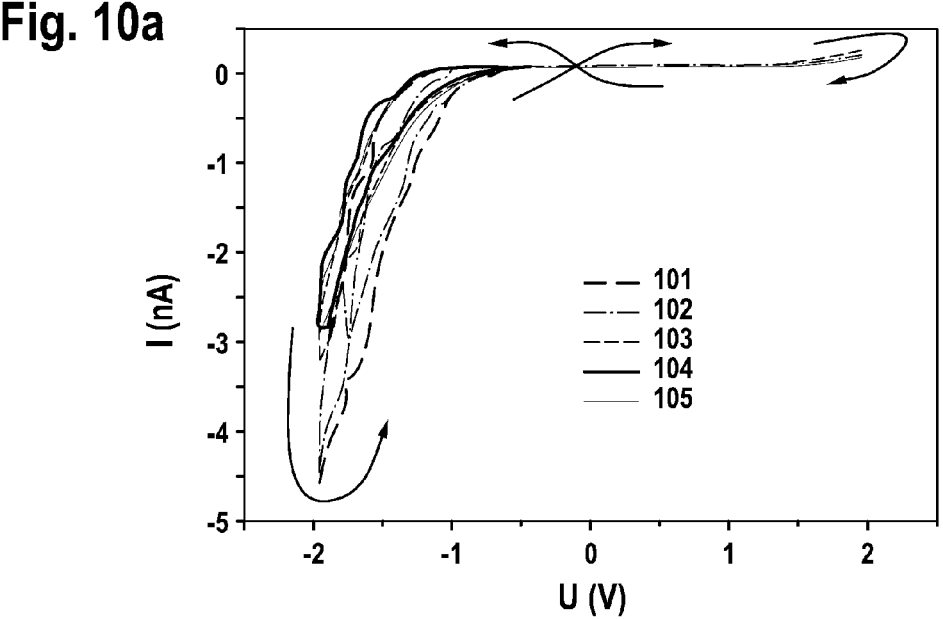
FIG. 10a shows the recorded current through a sample having a monolayer system produced from compound CCY-5-O3P with a permanent second electrode comprising Pb
Figure 10B:
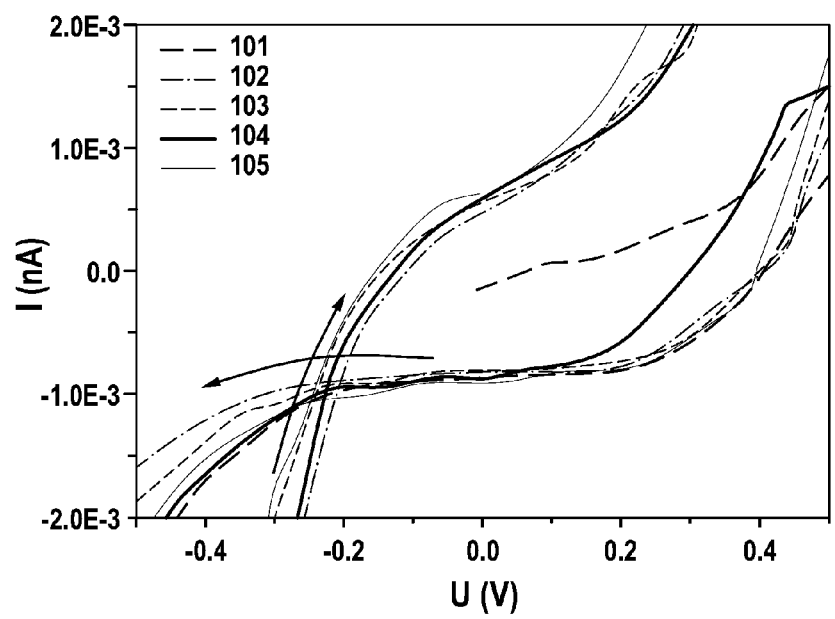
FIG. 10b shows an enlarged detail from FIG. 10a FIG. 11 shows resistances in the switched-on state (ON) and switched-off state (OFF) of a switching element according to the invention for a number of switching cycles.

FIG. 10a shows five selected current/voltage curves from 20 measurement cycles (101, 102, 103, 104 and 105) on a switching element measuring 50×50 µm² which has been produced as described above using CCY-5-O3P. The voltage was varied in accordance with FIG. 4 (triangular shape), in each cycle starting from 0 V to +2 V, from +2 V to 0 V, then from 0 V to −2 V and back to 0 V. FIG. 10b shows an enlargement of a section from FIG. 10a in the region of low pre-voltage. All curves apart from the first (beginning at 0 V and 0 A) are shifted towards 0 A owing to charging currents, in each case depending on the direction and speed of the change in voltage. As indicated by the arrows in FIG. 10a, the cyclic current/voltage curves show a clear, strongly asymmetrical memristive characteristic.

Figure 11:
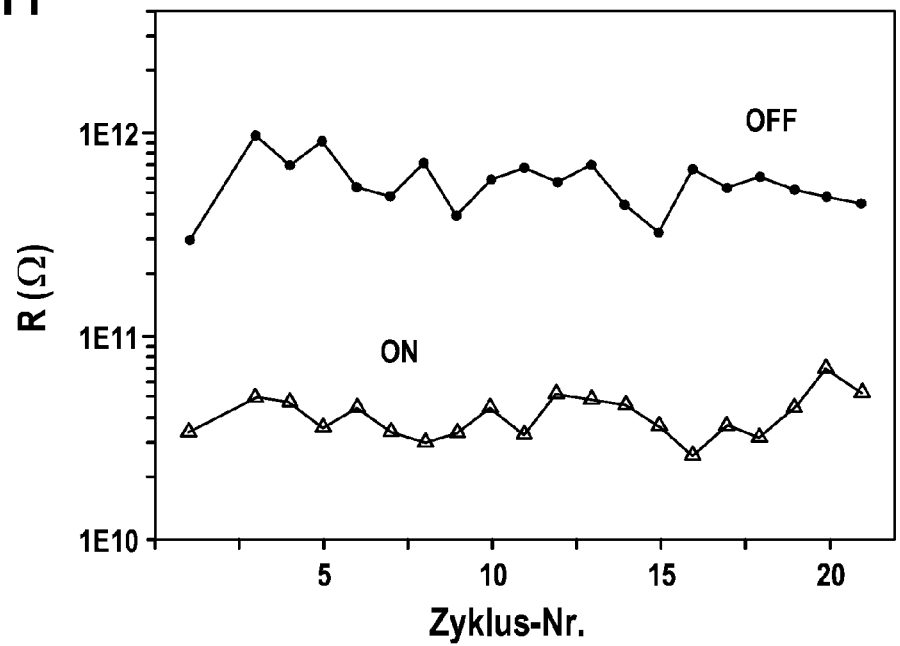

FIG. 11 shows the resistance values derived from the values of the 20 current/voltage curves depicted in FIG. 10b at low pre-voltages (linear regression from 0 V to −150 mV). The switching element investigated has constant resistance values from cycle to cycle within the scope of measurement accuracy. The resistance values in the switched-off state (OFF) are approximately a factor of 14 higher than in the switched-on state (ON). The switching elements are highly suitable for the production of memristive memories.

Figure 12:
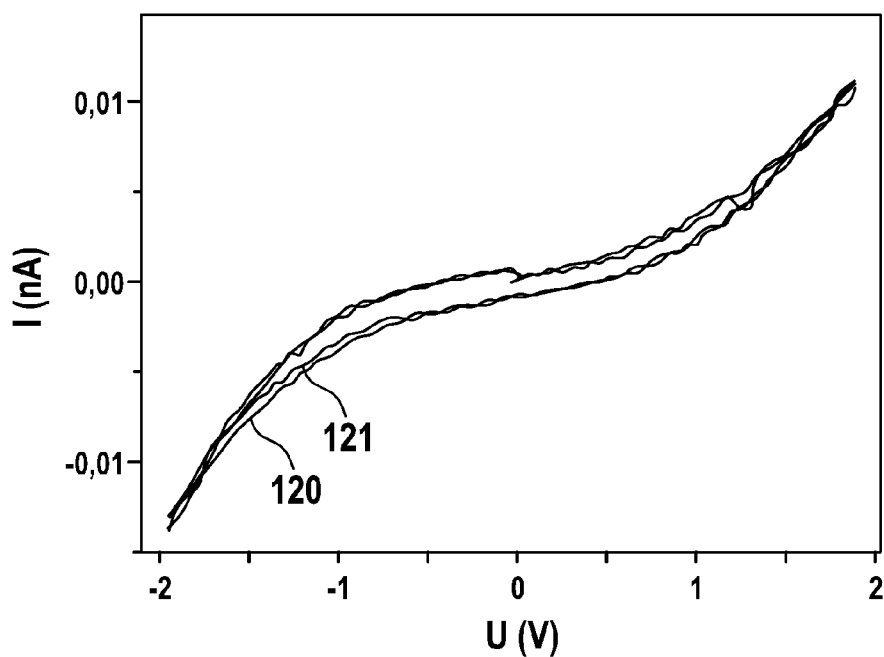
FIG. 12 shows a reference measurement with a non-switchable, nonpolar monolayer.

Reference Measurement:

FIG. 12 shows the recorded current for two cycles (120, 121) of the I/U characteristics of an alkylphosphonate-functionalised ("C18-PA") Si sample as passive reference system. No switching behaviour or hysteretic behaviour which is characteristic of memristive systems is observed. The week hysteresis over the entire voltage range can be attributed to capacitive charging currents. In particular, the resistance values remain constant at low reading voltages within the scope of measurement accuracy (=irrespective of the prehistory of the component).

Characterisation of Phosphonic Acid Monolayers on Titanium Nitride as Alternative Substrate Material for the First Electrode (20)

Production of the Monolayers

A p+-Si(100) wafer coated with a 30 nm layer of titanium nitride is divided into chips measuring 8 mm×8 mm and cleaned in acetone and isopropanol in an ultrasound bath for 5 min in each case. The chips are subsequently treated with oxygen plasma (200 W) for 3 min and immediately introduced into a 1 mM solution of CCY-5-O3P in tetrahydrofuran/methanol (1:1). After 72 h, the chips were removed from the solution, washed with ethanol and investigated.

The following properties were determined:

| Parameter | Comparison of TiN without SAM after plasma treatment | Properties of SAM on TiN |
| --- | --- | --- |
| Contact angle of water | <10° | 100-102° |
| Surface roughness | 0.28 nm | 0.31 nm (0.32 nm for C18 reference) |
| Layer thickness (ellipsometrically) | (none) | 1.2 ± 0.2 nm [1] |
| Change in work function (Kelvin probe) | Reference | −200 meV, in relation to reference |

[1] assumed refractive index n = 1.55

The values indicate successful derivatisation of the TiN surface with a self-arranged monolayer of CCY-5-O3P.

Characterisation of Phosphonic Acid Monolayers Using an Aluminium Oxide Interlayer on the First Electrode (20)

Production of the Monolayers

The starting material is a silicon wafer having a thickness of 525 μm and a diameter of 6 inches, with [100] orientation, which is strongly p-doped with boron and has a resistivity of about 0.005 Ω·cm.

The silicon wafer is coated with an $Al_2O_3$ layer having a thickness of about 2 nm by an ALD (atomic layer deposition) process. Before the deposition of $Al_2O_3$, the wafer was cleaned using the "RCA" wet-chemical cleaning method, which is known to the person skilled in the art, and dipped into 1% HF solution. Immediately thereafter, the wafer is transferred into a vacuum chamber, in which $Al_2O_3$ is deposited on the wafer surface with the aid of the precursor substances trimethylaluminium and water. After about 20 reaction cycles at 200° C., the desired layer thickness of 2 nm has been reached.

After the deposition of $Al_2O_3$, the wafer is divided into square parts ("chips") measuring 8 mm×8 mm. The chips are cleaned firstly in acetone and subsequently in isopropanol in an ultrasound bath for 5 min in each case. The chips are then treated with oxygen plasma (100 W, 1 min).

The chips are subsequently dipped into a solution (0.04 mmol) of the substance CY-5-O11P in THF. After 72 hours, the chip is removed from the solution, rinsed with THF, dried off using nitrogen, annealed at 120° C. in an oven for 24 hours, rinsed again with a 1:1 mixture of THF and methanol and dried off again using nitrogen.

After this pretreatment, the chips are characterised electrically using an Hg drop (32) as second electrode (FIG. 3). The first electrode is a copper block (30) which is conductively connected to the underside of the chips (strongly p-doped silicon).

Measurement Results

A direct voltage which varies over time in a cyclic sequence between a maximum negative voltage value (here −3 V) and a maximum positive voltage value (here −3 V) at a constant rate (here 20 mV/s) is applied to the two electrodes (30, 32) via the measuring instrument (34). FIG. 4 shows such a cycle (41). The resultant current through the sample (40) to be characterised is measured and recorded.

Figure 13:
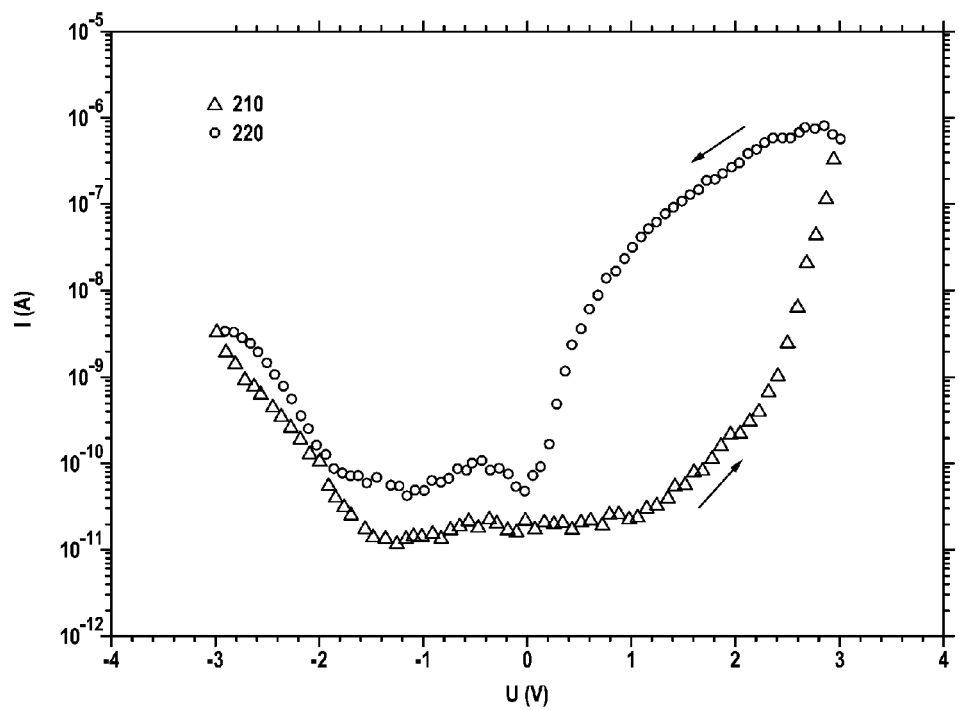
FIG. 13 shows the recorded current through a sample having a monolayer system produced from compound CY-5-O11P on Al$_2$O$_3$.
Figure 14:
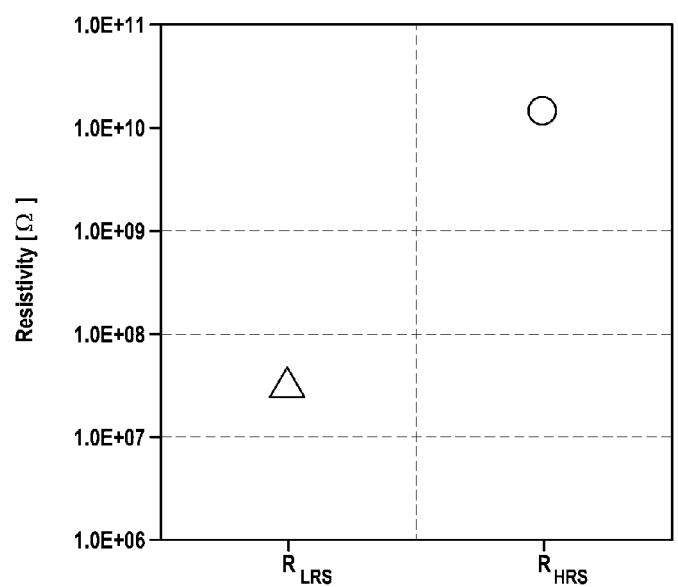
FIG. 14 shows states of high and low resistance of a sample having a monolayer system produced from compound CY-5-O11P on Al$_2$O$_3$.
Figure 15:
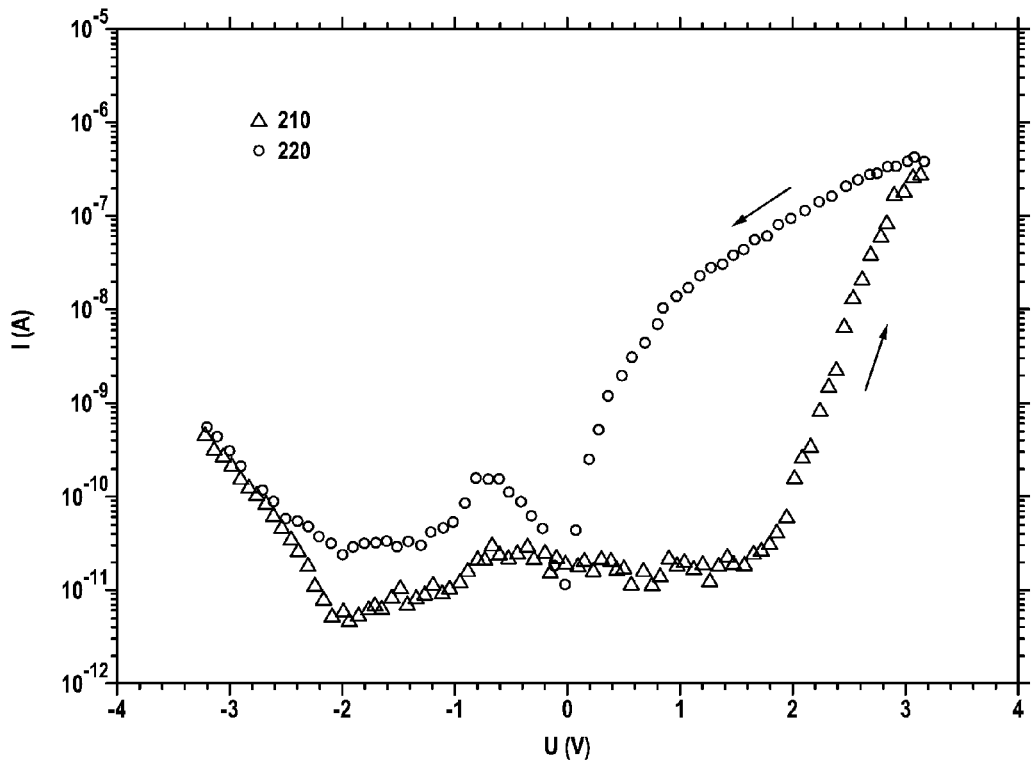
FIG. 15 shows a reference measurement with a non-switchable, non-fluorinated monolayer produced from compound CP-5-O11P.
Figure 16:
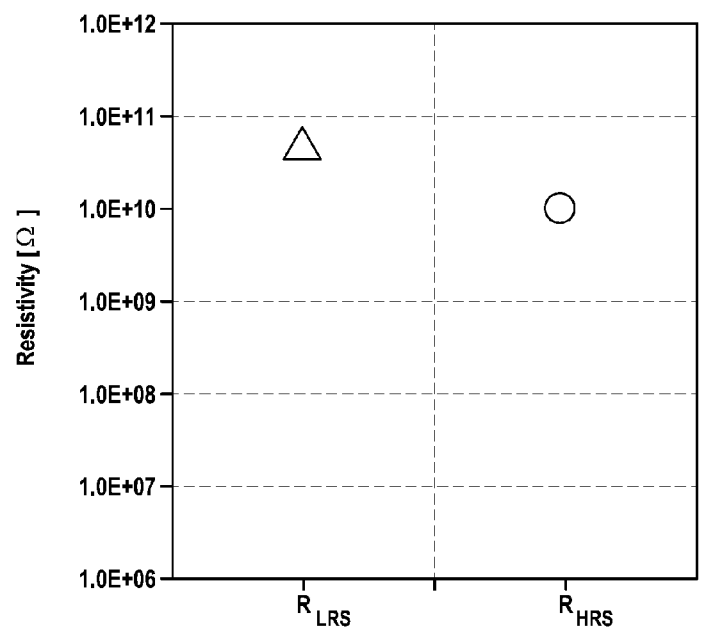
FIG. 16 shows states of constantly high resistance of a sample having a monolayer system produced from compound CP-5-O11P on Al$_2$O$_3$.

The recorded currents for various samples (40) are depicted in FIG. 13 and FIG. 15 and explained in greater detail below.

FIG. 13 shows the recorded current as a function of the applied voltage (current/voltage curve) through a sample (40) having the monolayer system CY-5-O11P. The current/voltage curve represents the average of the current values over three successive cycles.

A characteristic hysteretic behaviour in the region of positive pre-voltages of the substrate is evident. In the region of negative pre-voltages, lower currents than for positive pre-voltages and virtually no hysteretic behaviour are evident. The current/voltage characteristics resemble that of a diode. A diode-like behaviour, as can be seen in FIG. 13, is particularly desired for a memristive component within an integrated circuit.

The low currents measured here may be particularly advantageous for memory applications. Typical ON currents measured in the case of memristors based on the formation of metal filaments are very high (100 mA region) and represent a particular problem in electronic circuits (for example power consumption, evolution of heat).

The ratio, measured by means of an Hg electrode, between a state having relatively high resistance ($R_{HRS}$) and a state having relatively low resistance compared with the former, called the $R_{HRS}$:$R_{LRS}$ ratio below, is about 430 for the CY-5-O11P system. In order to determine the $R_{LRS}$ value, the voltage is increased from 0 V to 3 V and changed from 3 V back to 0 V. The voltage is subsequently varied in a cycle at constant rate (here 20 mV/s) with a maximum negative voltage of −0.1 V and a maximum positive voltage of 0.1 V. The resistance can be read off from the slope of the current/voltage curve of this voltage cycle. For the $R_{HRS}$ value, the voltage is changed from 0 V to −3 V, then from −3 V back to 0 V. The resistance is subsequently determined in an analogous manner as for the $R_{LRS}$ value. The $R_{LRS}$ and $R_{HRS}$ values for the CY-5-O11P monolayer system are plotted in FIG. 14.

The measurement described above for the determination of the resistances is independent of the measurement of the current/voltage curves shown in FIG. 13. The two measurements are separated by several minutes in which no voltage is applied to the component. The resistive states $R_{LRS}$ and $R_{HRS}$ are stable under ambient conditions. The results show that the system can be switched reversibly from a state having high resistance to a state having low resistance. The switching elements are thus suitable for the production of non-volatile, memristive memories.

Reference Measurement

As comparison, a sample (40) produced analogously was investigated using the non-laterally fluorinated reference compound CP-5-O11P. FIG. 15 shows the recorded and averaged current for three cycles of the current/voltage characteristics of a CP-5-O11P monolayer on an $Al_2O_3$-derivatised chip as unfluorinated reference system.

No state having low resistance and thus no switching behaviour which is characteristic of memristive systems is observed. The hysteresis over the entire voltage range can be attributed to capacitive charging currents. In particular, the resistance values (FIG. 16) remain constant at low reading voltages within the scope of measurement accuracy (independently of passing through a switching cycle in accordance with FIG. 15).

LIST OF REFERENCE NUMBERS 1 switching element
10 electronic component (with crossbar array)
12 outer substrate
14 insulator
16 second electrode
18 molecular layer
20 first electrode
22 diode
24 n+ layer
26 p+ layer
30 copper plate
32 Hg drop
34 measuring instrument
36 current measuring unit
38 voltage source
40 sample
41 measurement cycle
50 first sample
51 second sample
52 third sample
70 resistance
71 voltage
90 contact needle
101 1st cycle
102 5th cycle
103 10th cycle
104 15th cycle
105 20th cycle
120 1st cycle
121 2nd cycle
160 contact area of the second electrode
200 contact area of the first electrode
210 rising pre-voltage
220 falling pre-voltage

The invention claimed is:
1. A compound of formula I

$$R^1\text{-}(A^1\text{-}Z^1)_r\text{—}B^1\text{—}(Z^2\text{-}A^2)_s\text{-Sp-G} \qquad (I)$$

in which
G denotes —SO$_2$OH, —OP(O)(OH)$_2$, —P(O)(OH)$_2$, —C(OH)(PO(OH)$_2$)$_2$, —Si(OR$^x$)$_3$ or —SiCl$_3$,
R$^1$ denotes H, an alkyl or alkoxy radical having 1 to 15 C atoms, where, in addition, one or more CH$_2$ groups in these radicals may each be replaced, independently of one another, by —C≡C—, —CH=CH—,

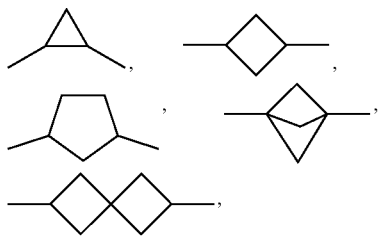

—O—, —S—, —CF$_2$O—, —OCF$_2$—, —CO—O—, or —O—CO—, —SiR$^o$R$^{oo}$—, —NH—, —NR$^o$— or —SO$_2$— in such a way that O atoms are not linked directly to one another, and in which, in addition, one or more H atoms may each be replaced by halogen, CN, SCN or SF$_5$, R$^o$, R$^{oo}$, identically or differently, denote an alkyl or alkoxy radical having 1 to 15 C atoms, in which, in addition, one or more H atoms may each be replaced by halogen, A$^1$, A$^2$ on each occurrence, identically or differently, denote an aromatic, heteroaromatic, alicyclic or heteroaliphatic ring having 4 to 25 ring atoms, which may also contain condensed rings and which may be mono- or polysubstituted by Y•

Y on each occurrence, identically or differently, denotes F, Cl, CN, SCN, SF$_5$ or straight-chain or branched, in each case optionally fluorinated alkyl, alkoxy, alkylcarbonyl, alkoxycarbonyl, alkylcarbonyloxy or alkoxycarbonyloxy having 1 to 12 C atoms, B$^1$ denotes

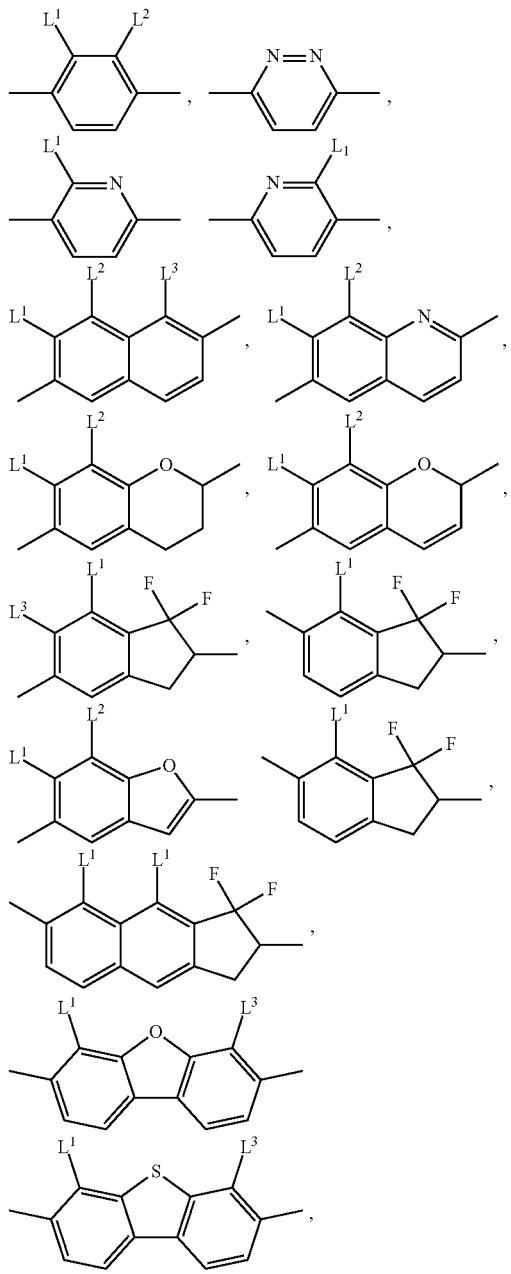

-continued

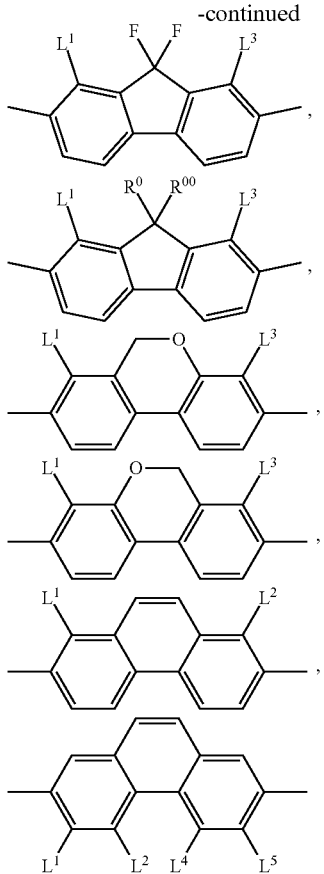

where the groups may be oriented in both directions,
$L^1$ to $L^5$, independently of one another, denote F, Cl, Br, I, CN, $SF_5$, $CF_3$ or $OCF_3$, where $L^3$ may alternatively also denote H,
$Z^1$, $Z^2$ on each occurrence, identically or differently, denote a single bond, —$CF_2O$—, —$OCF_2$—, —$CF_2S$—, —$SCF_2$—, —$CH_2O$—, —$OCH_2$—, —C(O)O—, —OC(O)—, —C(O)S—, —SC(O)—, —$CH_2$—, —$(CH_2)_2$—, —$(CH_2)_3$—, —$(CH_2)_4$—, —$CF_2$—, —$CF_2$—$CF_2$—, —$CF_2$—$CH_2$—, —$CH_2$—$CF_2$—, —CH=CH—, —CF=CF—, —CF=CH—, —CH=CF—, —$(CH_2)_3O$—, —$O(CH_2)_3$—, —C≡C—, —O—, —S—, —C=N—, —N=C—, —N=N—, —N=N(O)—, —N(O)=N— or —N=C—C=N—,
Sp denotes a spacer group or a single bond,
$R^x$ denotes straight-chain or branched alkyl having 1 to 6 C atoms, and
r and s, independently of one another, denote 0, 1, 2 or 3, where r+s≤4; and
wherein the compound of formula I is mesogenic and has negative dielectric anisotropy.

2. The compound according to claim 1, wherein Y, on each occurrence, is F or Cl.

3. The compound according to claim 1, wherein $L^1$ to $L^5$, independently of one another, denote Cl or F, and $L^3$ may alternatively also denote H.

4. The compound according to claim 1, wherein the compound of formula I is selected from sub-formulae Ia to If:

R¹—B¹-Sp-G    Ia

R¹-(A¹-Z¹)—B¹-Sp-G    Ib

R¹-(A¹-Z¹)₂—B¹-Sp-G    Ic

R¹—B¹—(—Z²-A²)-Sp-G    Id

R¹—B¹—(Z²-A²)₂-Sp-G    Ie

R¹-(A¹-Z¹)—B¹—(Z²-A²-)-Sp-G    If wherein
A¹ and
each independently denote

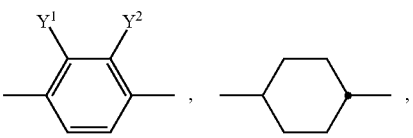

B¹
denotes

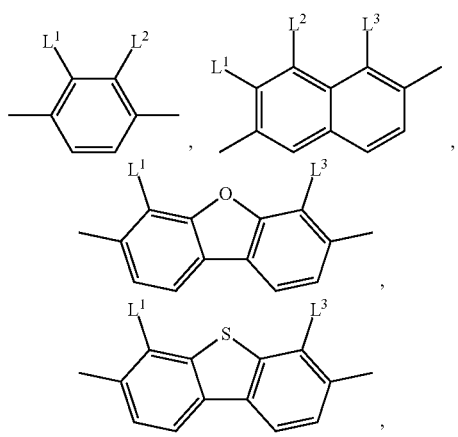

where the groups may be oriented in either direction,
$R^1$ denotes alkyl having 1-15 C atoms,
$L^1$ and $L^2$, independently of one another, denote Cl or F, where at least one of the radicals $L^1$ and $L^2$ denotes F,
$L^3$ denotes F,
$Y^1$ and $Y^2$ independently of one another, denote H, Cl or F,
$Z^1$ and $Z^2$ independently of one another, denote a single bond, —$CF_2O$—, —$OCF_2$—, —$CH_2O$—, $OCH_2$— or —$CH_2CH_2$—,
Sp denotes unbranched 1, ω-alkylene having 1 to 12 C atoms, and
G denotes —$SO_2OH$, —$OP(O)(OH)_2$, —$PO(OH)_2$, —$COH(PO(OH)_2)_2$, —$Si(OR)_3$ or —$SiCl_3$.

5. The compound according to claim 4, wherein Sp denotes unbranched 1,ω-perfluoroalkylene having 1 to 12 C atoms.

6. The compound according to claim 4, wherein the compound of formula I is selected from sub-formulae Ia, Ib and Id.

7. The compound according to claim 4, wherein G is —$OP(O)(OH)_2$, —$P(O)(OH)_2$, or —$C(OH)(PO(OH)_2)_2$.

8. The compound according to claim 1, wherein G is —$OP(O)(OH)_2$, —$P(O)(OH)_2$, or —$C(OH)(PO(OH)_2)_2$.

9. A compound of formula I

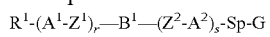

in which

Sp denotes —O(CF$_2$)$_{p1}$— or —(CF$_2$)$_{p1}$—,
p1 denotes an integer from 1 to 12,
R$^1$ denotes H, an alkyl or alkoxy radical having 1 to 15 C atoms, where, in addition, one or more CH$_2$ groups in these radicals may each be replaced,

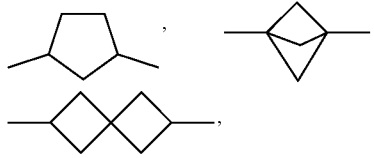

—O—, —S—, —CF$_2$O—, —OCF$_2$—, —CO—O—, or —O—CO—, —SiR$^0$R$^{00}$—, —NH—, —NR$^0$— or —SO$_2$— in such a way that O atoms are not linked directly to one another, and in which, in addition, one or more H atoms may each be replaced by halogen, CN, SCN or SF$_5$, R$^0$, R$^{00}$, identically or differently, denote an alkyl or alkoxy radical having 1 to 15 C atoms, in which, in addition, one or more H atoms may each be replaced by halogen, A$^1$, A$^2$ on each occurrence, identically or differently, denote an aromatic, heteroaromatic, alicyclic or heteroaliphatic ring having 4 to 25 ring atoms, which may also contain condensed rings and which may be mono- or polysubstituted by Y•

Y on each occurrence, identically or differently, denotes F, Cl, CN, SCN, SF$_5$ or straight-chain or branched, in each case optionally fluorinated alkyl, alkoxy, alkylcarbonyl, alkoxycarbonyl, alkylcarbonyloxy or alkoxycarbonyloxy having 1 to 12 C atoms, B$^1$ denotes

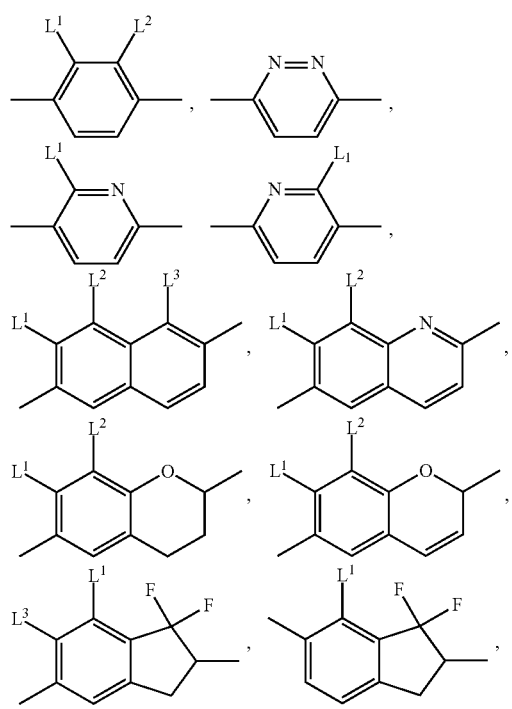

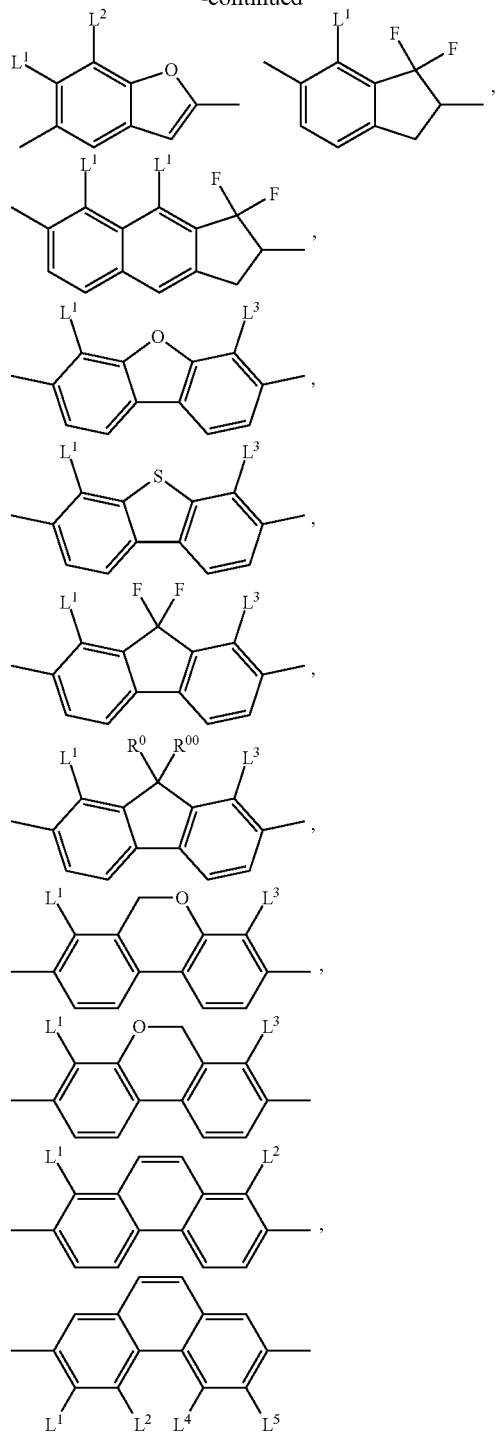

where the groups may be oriented in both directions,

L$^1$ to L$^5$, independently of one another, denote F, Cl, Br, I, CN, SF$_5$, CF$_3$ or OCF$_3$, where L$^3$ may alternatively also denote H, Z$^1$, Z$^2$ on each occurrence, identically or differently, denote a single bond, —CF$_2$O—, —OCF$_2$—, —CF$_2$S—, —SCF$_2$—, —CH$_2$O—, —OCH$_2$—, —C(O)O—, —OC(O)—, —C(O)S—, —SC(O)—, —CH$_2$—, —(CH$_2$)$_2$—, —(CH$_2$)$_3$—, —(CH$_2$)$_4$—, —CF$_2$—, —CF$_2$—CF$_2$—, —CF$_2$—CH$_2$—, —CH$_2$—CF$_2$—, —CH=CH—, —CF=CF—, —CF=CH—, —CH=CF—, —(CH$_2$)$_3$O—, —O(CH$_2$)$_3$—, —C≡C—, —O—, —S—, —C=N—, —N=C—, —N=N—, —N=N(O)—, —N(O)=N— or —N=C—C=N—, Sp denotes a spacer group or a single bond, G denotes —SO$_2$OH, —OP(O)(OH)$_2$, —PO(OH)$_2$, —C(OH)(PO(OH)$_2$)$_2$, Si(OR$^x$)$_3$ or —SiCl$_3$, R$^x$ denotes straight-chain or branched alkyl having 1 to 6 C atoms, and r and s, independently of one another, denote 0, 1, 2 or 3, where r+s≤4; and wherein the compound of formula I is mesogenic and has negative dielectric anisotropy.

10. The compound according to claim 9, wherein Y, on each occurrence, is F or Cl.

11. The compound according to claim 9, wherein L$^1$ to L$^5$, independently of one another, denote Cl or F, and L$^3$ may alternatively also denote H.

12. The compound according to claim 9, wherein G is —OP(O)(OH)$_2$, —P(O)(OH)$_2$, or —C(OH)(PO(OH)$_2$)$_2$.

* * * * *